United States Patent
Ryan et al.

(10) Patent No.: US 9,504,568 B2
(45) Date of Patent: Nov. 29, 2016

(54) REPLACEMENT PROSTHETIC HEART VALVES AND METHODS OF IMPLANTATION

(75) Inventors: Timothy R. Ryan, Shorewood, MN (US); Philipp Bonhoeffer, London (GB)

(73) Assignee: Medtronic, Inc., Minneapolis, MN (US)

(*) Notice: Subject to any disclaimer, the term of this patent is extended or adjusted under 35 U.S.C. 154(b) by 1682 days.

(21) Appl. No.: 12/070,387

(22) Filed: Feb. 15, 2008

(65) Prior Publication Data
US 2008/0243246 A1    Oct. 2, 2008

Related U.S. Application Data

(60) Provisional application No. 60/901,787, filed on Feb. 16, 2007.

(51) Int. Cl.
*A61F 2/24*    (2006.01)
*A61F 2/958*   (2013.01)

(52) U.S. Cl.
CPC ........... *A61F 2/2436* (2013.01); *A61F 2/2418* (2013.01); *A61F 2/2433* (2013.01); *A61F 2/24* (2013.01); *A61F 2/2409* (2013.01); *A61F 2/958* (2013.01); *A61F 2210/0014* (2013.01); *A61F 2220/005* (2013.01); *A61F 2230/0054* (2013.01); *A61F 2230/0069* (2013.01)

(58) Field of Classification Search
CPC .......................................... A61F 2/24
USPC .................................. 623/2.18, 900
See application file for complete search history.

(56) References Cited

U.S. PATENT DOCUMENTS

| | | |
|---|---|---|
| 3,334,629 A | 8/1967 | Cohn |
| 3,409,013 A | 11/1968 | Berry |
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |

(Continued)

FOREIGN PATENT DOCUMENTS

| | | |
|---|---|---|
| CN | 2007-100074433 | 8/2007 |
| DE | 3640745 | 6/1987 |

(Continued)

OTHER PUBLICATIONS

Bonhoeffer, et al, "Transcatheter Implantation of a Bovine Valve in Pulmonary Position," Circulation, 2002; 102:813-816.

(Continued)

*Primary Examiner* — Jacqueline Woznicki

(57) ABSTRACT

A replacement prosthetic heart valve for engagement with a structure of a previously implanted prosthetic heart valve. The replacement heart valve includes a stent structure including a generally tubular body portion with an interior area and a series of wire portions arranged in a mesh-like configuration, and at least one stent post engaging structure extending radially outwardly from the body portion for engaging with an outer surface of a stent post of the previously implanted prosthetic heart valve. The stent structure further includes at least two leaflets attached within the interior area of the tubular body portion of the stent structure.

19 Claims, 12 Drawing Sheets

(56) References Cited

U.S. PATENT DOCUMENTS

| | | |
|---|---|---|
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A * | 3/1995 | Pavcnik et al. .............. 623/2.35 |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A * | 1/1999 | Bessler et al. .............. 623/2.38 |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 * | 1/2001 | Andersen et al. ............ 623/1.26 |
| 6,171,335 B1 | 1/2001 | Wheatley et al. |
| 6,176,875 B1 * | 1/2001 | Lenker et al. ................ 623/1.49 |
| 6,200,336 B1 | 3/2001 | Pavcnik et al. |
| 6,203,550 B1 | 3/2001 | Olson |
| 6,210,408 B1 | 4/2001 | Chandrasekaran et al. |

(56) References Cited

U.S. PATENT DOCUMENTS

| | | |
|---|---|---|
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 * | 6/2005 | Cribier ................. 623/2.11 |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,128,759 B2 | 10/2006 | Osborne et al. |
| 7,147,661 B2 * | 12/2006 | Chobotov et al. ........... 623/1.16 |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Schreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,682,390 B2 | 3/2010 | Seguin |
| 7,780,726 B2 | 8/2010 | Seguin |
| 7,806,919 B2 | 10/2010 | Bloom et al. |
| 7,871,436 B2 * | 1/2011 | Ryan .................. A61F 2/2418 623/1.15 |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |

(56) References Cited

U.S. PATENT DOCUMENTS

| | | |
|---|---|---|
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1* | 10/2002 | Garrison et al. ............ 623/2.11 |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0120338 A1* | 6/2003 | Chobotov et al. ............ 623/1.36 |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093075 A1 | 5/2004 | Kuehne |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Lobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0251251 A1 | 11/2005 | Cribier |
| 2005/0261759 A1 | 11/2005 | Lambrecht et al. |

(56) References Cited

U.S. PATENT DOCUMENTS

| | | |
|---|---|---|
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1* | 3/2006 | Revuelta et al. ............ 623/2.18 |
| 2006/0058775 A1 | 3/2006 | Stevens et al. |
| 2006/0058872 A1 | 3/2006 | Salahich et al. |
| 2006/0074484 A1 | 4/2006 | Huber |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0149360 A1 | 7/2006 | Schwammenthal et al. |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0112422 A1 | 5/2007 | Dehdashtian |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1* | 1/2008 | Vesely ............................ 623/2.1 |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1* | 3/2008 | Tuval ................... A61F 2/2418 623/2.1 |
| 2008/0071362 A1* | 3/2008 | Tuval ................... A61F 2/2418 623/2.1 |
| 2008/0071363 A1* | 3/2008 | Tuval ................... A61F 2/2418 623/2.1 |
| 2008/0071366 A1* | 3/2008 | Tuval ................... A61F 2/2418 623/2.11 |
| 2008/0071368 A1* | 3/2008 | Tuval ................... A61F 2/2418 623/2.17 |
| 2008/0071369 A1* | 3/2008 | Tuval ................... A61F 2/2418 623/2.38 |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Stryc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1* | 1/2009 | Goetz et al. .................. 623/2.18 |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0164006 A1 | 6/2009 | Seguin et al. |
| 2009/0171447 A1 | 7/2009 | VonSeggesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1* | 8/2009 | Straubinger ........... A61F 2/2418 623/1.17 |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2009/0287299 A1* | 11/2009 | Tabor ..................... A61F 2/013 623/1.26 |
| 2010/0004740 A1 | 1/2010 | Seguin et al. |
| 2010/0030328 A1 | 2/2010 | Seguin et al. |

(56) References Cited

U.S. PATENT DOCUMENTS

| | | |
|---|---|---|
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 10 074 | 10/2001 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| EP | 1 671 608 | 6/2006 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/44313 | 8/2000 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 2004/019825 | 3/2004 |
| WO | 2004/089250 | 10/2004 |
| WO | 2005/004753 | 1/2005 |
| WO | 2005/046528 | 5/2005 |
| WO | 2006/026371 | 3/2006 |
| WO | WO 2007/013999 | 2/2007 |
| WO | 2007/053243 | 5/2007 |
| WO | WO 2007/071436 | 6/2007 |
| WO | 2007/081820 | 7/2007 |
| WO | 2007/130537 | 11/2007 |
| WO | 2008/047354 | 4/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/111241 | 9/2009 |

OTHER PUBLICATIONS

Bonhoeffer, et al., "Percutaneous Insertion of the Pulmonary Valve," J. Am. Coll. Cardiol., 2002; 39:1664-1669.

Cribier, et al., "Percutaneous Transcatheter Implantation of an Aortic Valve Prosthesis for Calcific Aortic Stenosis," Circulation, 202; 106:3006-3008.

Boudjemline, et al., "New insights in minimally invasive valve replacement: description of a cooperative approach for the off-pump replacement of mitral valves," European Heart Journal (2005) 26, 2013-2017.

Walther, et al., "Valve-in-a-Valve Concept for Transcatheter Minimally Invasive Repeat Xenograft Implantation," JACC, vol. 50, No. 1, 2007, Jul. 3, 2007:56-60.

Andersen, H.R. et al., "Transluminal implantation of artificial heart valves. Description of a new expandable aortic valve and initial results with implantation by catheter technique in closed chest pigs." Euro. Heart J. (1992) 13:704-708.

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. Volume II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

(56) References Cited

OTHER PUBLICATIONS

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, pp. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. 1. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Ma, Ling, et al., "Double-crowned valved stents for off-pump mitral valve replacement," European Journal of Cardio Thoracic Surgery, 28:194-198, 2005.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Pelton et al., "Medical Uses of Nitinol," Materials Science Forum vols. 327-328, pp. 63-70 (2000).

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Stassano et al., "Mid-term results of the valve-on-valve technique for bioprosthetic failure," Eur. J. Cardiothorac. Surg. 2000; 18:453-457.

Pavcnik et al., "Aortic and venous valve for percutaneous insertion," Min. Invas. Ther. & Allied Techol. 2000, vol. 9, pp. 287-292.

* cited by examiner

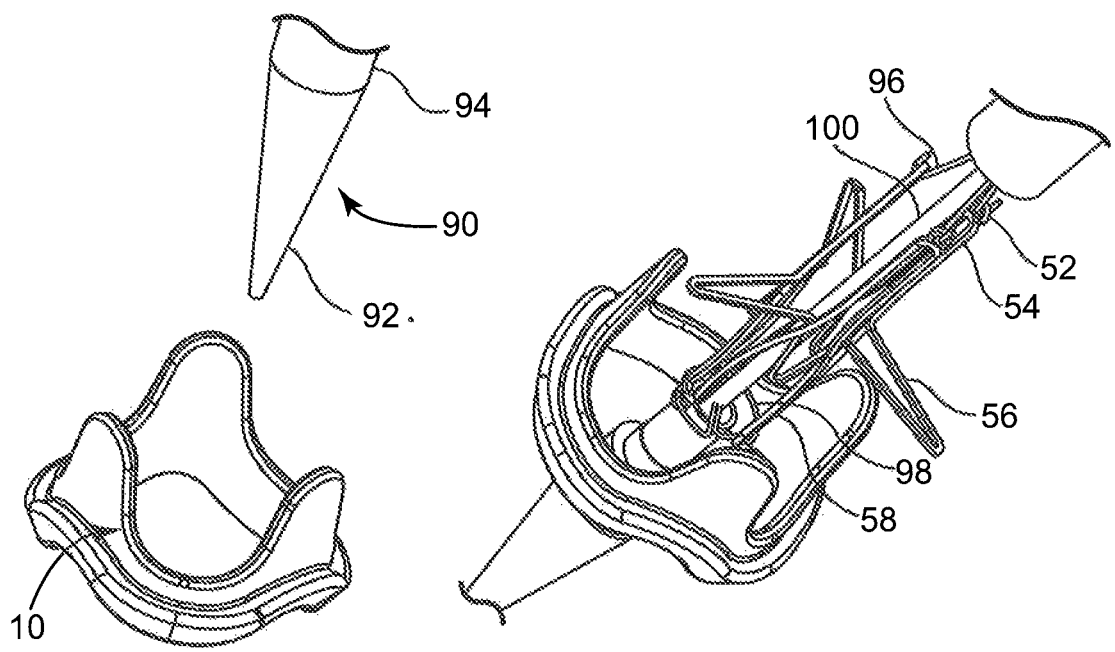
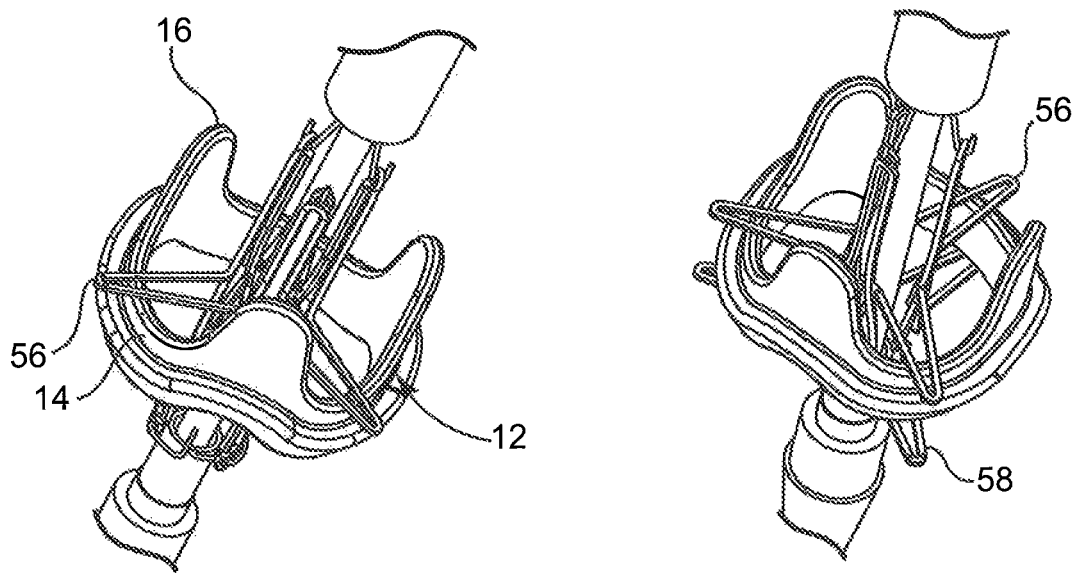
Fig. 7   Fig. 8
Fig. 9   Fig. 10

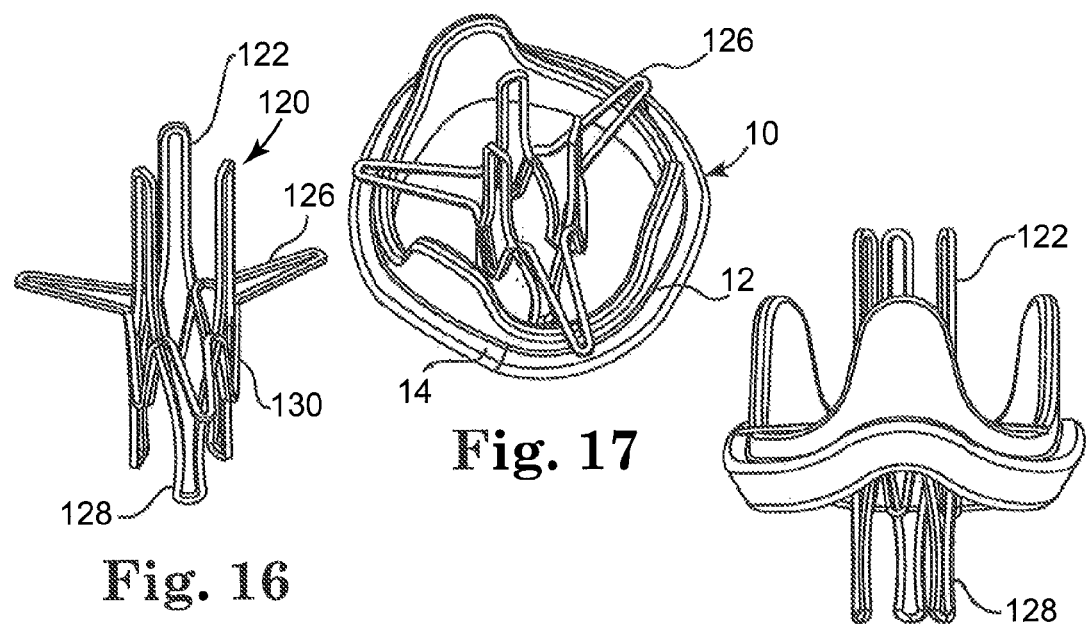
Fig. 16
Fig. 17
Fig. 18
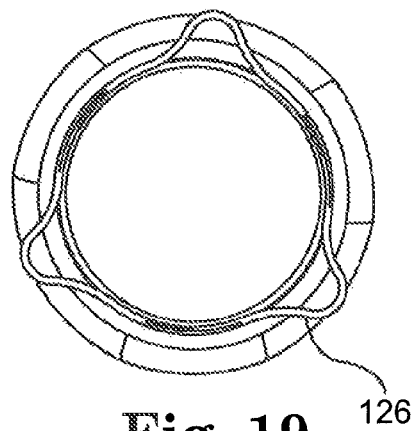
Fig. 19
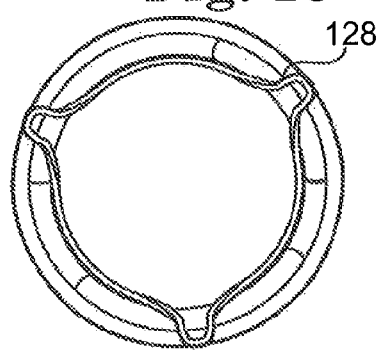
Fig. 20
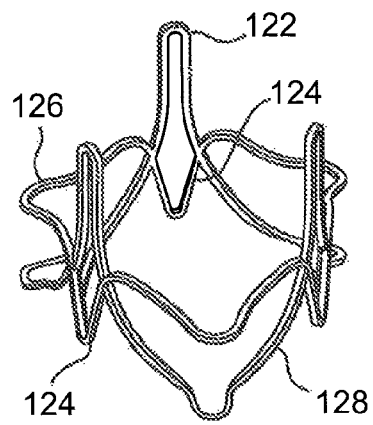
Fig. 21
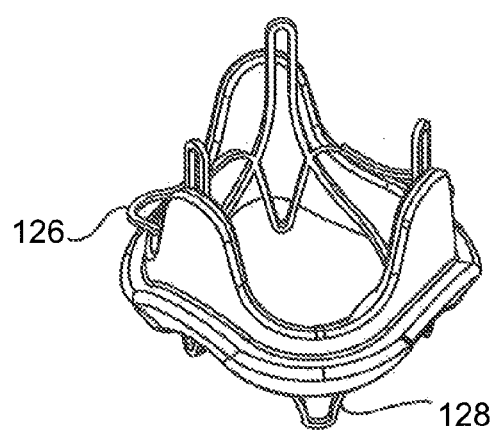
Fig. 22

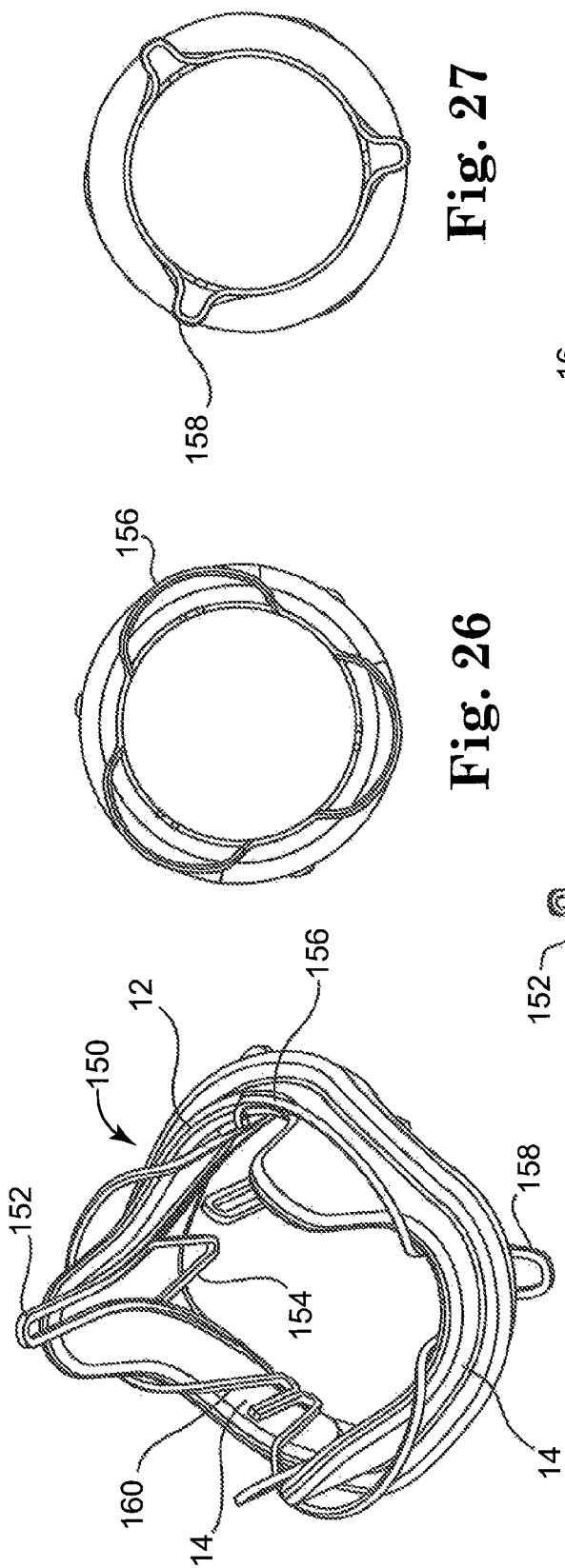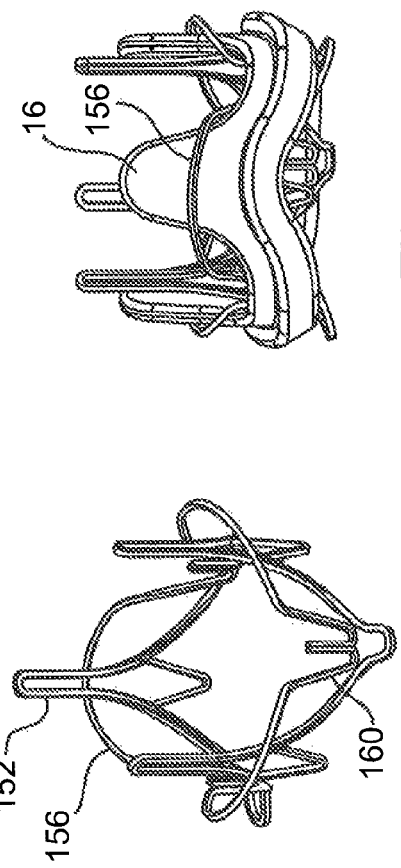

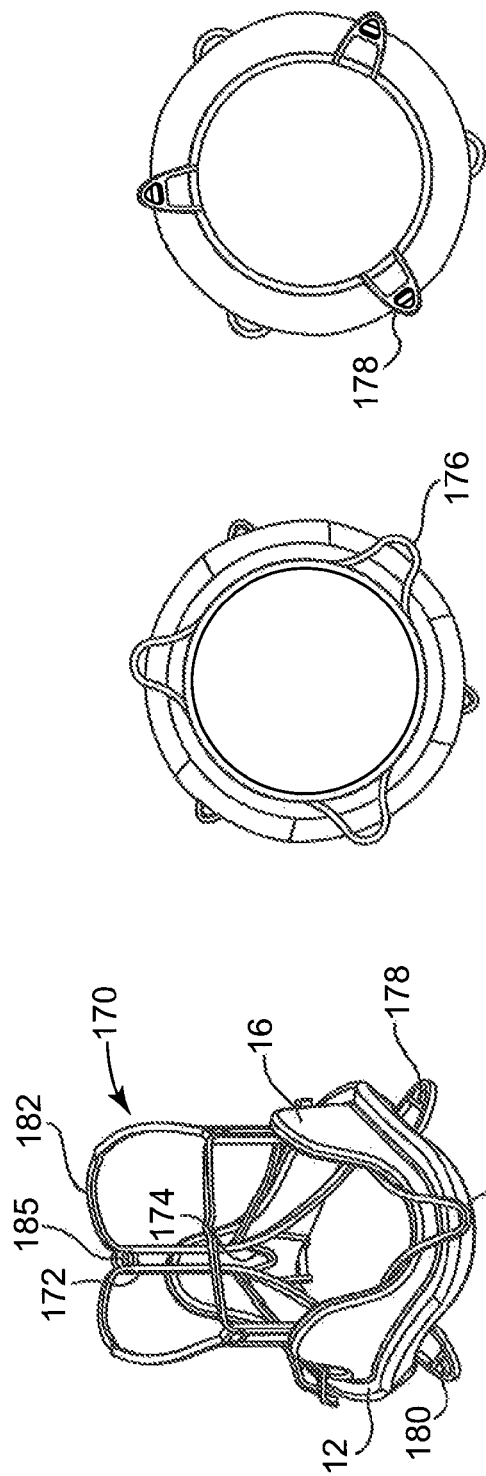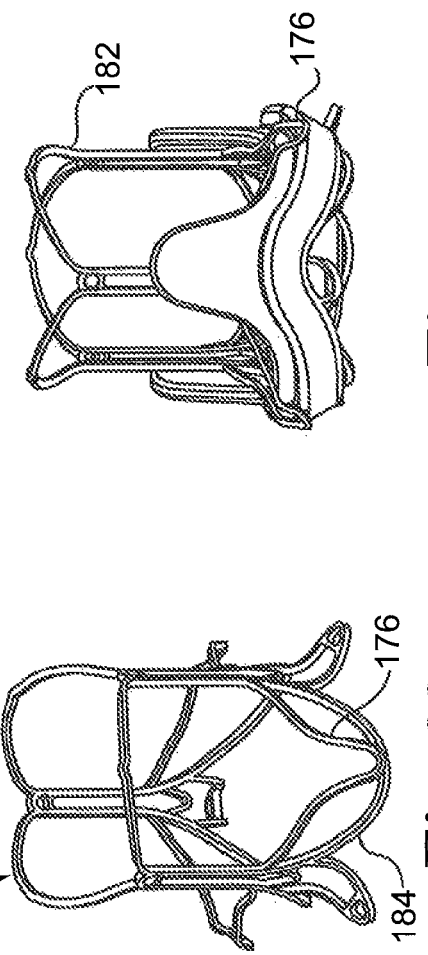

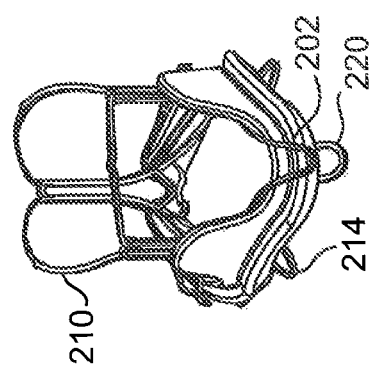
Fig. 35
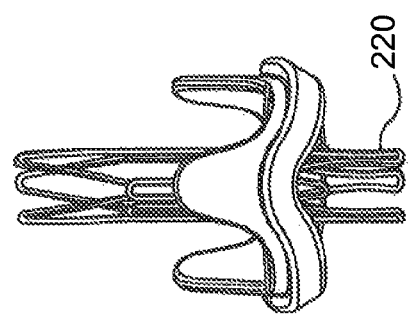
Fig. 36
Fig. 37
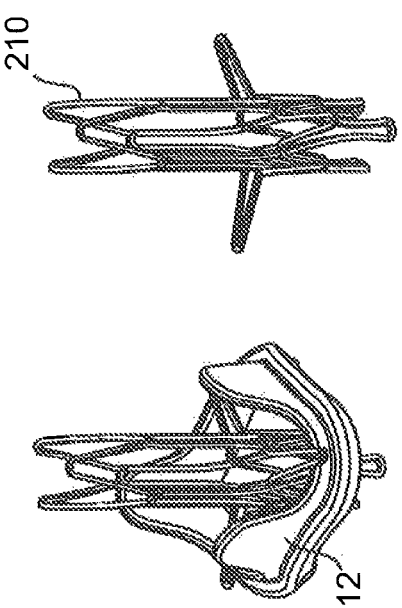
Fig. 38
Fig. 39
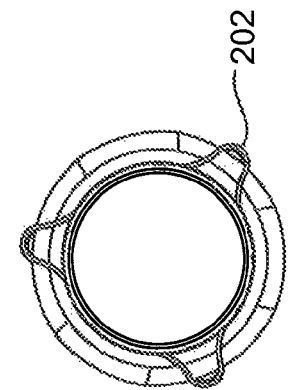
Fig. 40
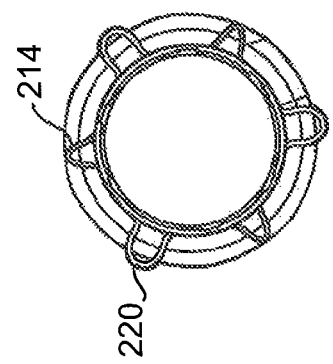
Fig. 41
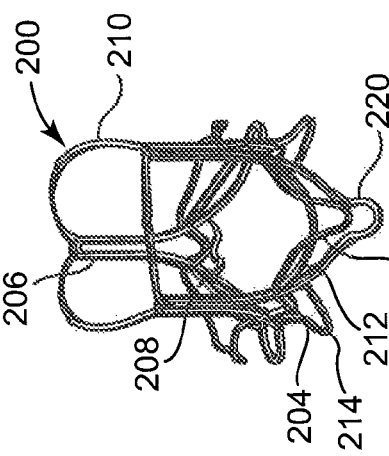

REPLACEMENT PROSTHETIC HEART VALVES AND METHODS OF IMPLANTATION

CROSS-REFERENCE TO RELATED APPLICATION

The present application claims priority to U.S. Provisional Application No. 60/901,787, filed Feb. 16, 2007, and titled "Replacement Prosthetic Heart Valve Including Delivery System and Method of Implantation", the entire contents of which is incorporated herein by reference in its entirety.

TECHNICAL FIELD

The present invention relates to prosthetic heart valves. More particularly, it relates to devices, methods, and delivery systems for percutaneously implanting prosthetic heart valves.

BACKGROUND

Various types and configurations of prosthetic heart valves are used to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses.

As used throughout this specification a "prosthetic heart valve" is intended to encompass bioprosthetic heart valves having leaflets made of a biological material (e.g., harvested porcine valve leaflets, or bovine or equine pericardial leaflets), along with synthetic leaflet materials or other materials. These bioprosthetic heart valves typically include a stent having a substantially circular base (or stent ring), around which an annular suture material is disposed for suturing the prosthesis to heart tissue. The stent further typically includes at least two, but typically three, support structures extending from the stent ring. These support structures are commonly referred to as stent posts or commissure posts. These posts typically are rigid yet somewhat flexible structures extending from the stent ring, which are covered by a cloth-like material similar to that of the annular suture material. The stent or commissure posts define the juncture between adjacent tissue or synthetic leaflets otherwise secured thereto. Examples of bioprosthetic heart valves are described in U.S. Pat. No. 4,106,129 (Carpentier et al.), and U.S. Pat. No. 5,037,434 (Lane), the entire disclosures of which are incorporated herein by reference. These disclosures describe a conventional configuration of three leaflets, with one leaflet disposed between each pair of stent or commissure posts. Regardless of whether a stent is provided, however, bioprosthetic heart valves are generally tubular so that when the leaflets are in an open position, an internal passage is defined through which blood can flow.

The bioprosthetic heart valves further typically include a sewing ring or suture ring that provides a means for fixing the prosthetic heart valve to the patient's native heart valve orifice tissue (e.g., native annulus or valvular rim) that is associated with the native heart valve being repaired or replaced. In particular, an exacting surgical implantation technique is traditionally employed whereby the heart is stopped (i.e., cardiopulmonary bypass) and opened, which is followed by surgical removal of damaged or diseased natural valve structure. A prosthetic heart valve can then be oriented within the native valvular area, with the sewing ring being seated against or at the native annulus or valvular rim. Sutures are then used to affix the sewing ring to the natural tissue. Obviously, the risks associated with this invasive type of surgery are numerous, particularly when cardiopulmonary bypass procedures are used.

A successfully implanted prosthetic heart valve will normally function without problems for many years. In certain instances, however, deficiencies may become evident shortly after implant or within a few years, particularly in younger patients. Common functional deficiencies include the calcification of the prosthetic heart valve leaflets, stenosis, and prosthetic heart valve insufficiency. Under these and other circumstances, the prosthetic heart valve does not function properly and conventionally requires surgical removal and replacement. Surgical removal of such a previously implanted prosthetic heart valve entails the same invasive surgical intervention described above, coupled with the need to remove the old prosthetic valve and implant a new prosthetic heart valve. In addition, the risk of mortality is often higher when performing a second surgery in the same area of the body, particularly when performing heart-related surgeries. Another disadvantage to this additional surgery is that the reopening of a sternotomy has been known to have a relatively high risk of causing an infection.

Thus, while these types of surgeries are well-accepted, the conventional surgical intervention described above is difficult to perform and can result in patient injury or more severe complications. In fact, due to physical weakness of a patient, implantation of a prosthetic heart valve via the conventional surgical technique may be considered too high-risk or contra-indicated for certain patients. Further, removal of a previously implanted prosthetic heart valve requires cutting of the sutures that secure the prosthesis to the native annulus/valvular rim, and attachment of a new sewing ring via stitching, which can further compromise the integrity of the valvular rim and lead to recovery complications, morbidity, and mortality.

Although not necessarily related to the specific prosthetic heart valve replacement concerns described above, efforts have also been made to devise a prosthetic heart valve capable of being delivered percutaneously via transcatheter implantation, thereby avoiding the complications and risks associated with conventional surgical intervention. For example, in U.S. Pat. No. 6,168,614 (Andersen et al.), a heart valve prosthesis is described for implantation in the body by use of a catheter. The valve prosthesis consists of a support structure with a tissue valve connected to it, whereby the support structure is delivered in a collapsed state through a blood vessel and secured to a desired valve location with the support structure in an expanded state.

Other percutaneously-delivered prosthetic heart valves have been suggested having a generally similar configuration, such as by Bonhoeffer, P. et al., "*Transcatheter Implantation of a Bovine Valve in Pulmonary Position.*" Circulation, 2002; 102:813-816, and by Cribier, A. et al. "*Percutaneous Transcatheter Implantation of an Aortic Valve Prosthesis for Calcific Aortic Stenosis.*" Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and any balloons used to expand the stent. Thus, with these transcatheter techniques, conventional sewing of the prosthetic heart valve to the patient's native tissue is not necessary. Similarly, in an article by Bonhoeffer, P. et al. titled "*Percutaneous Insertion of the Pulmonary Valve.*" J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Devices and methods have more recently been developed for percutaneously replacing deficient, previously implanted prosthetic heart valves, which are described, for example, in U.S. Patent Publication No. 2006/0052867 (Revuelta et al.), the entire disclosure of which is incorporated herein by reference. Other transcatheter technologies for delivering replacement valves are described in PCT Application Nos. WO 2007/053243-A2, WO 2007/130537-A1, and WO 2007/081820-A1; United States Patent Application Publication Nos. 2005/0251251-A1, 2007/0043435-A1, and 2008/0004696-A1; and U.S. Pat. No. 7,195,641. However, a need exists for additional prosthetic heart valves, delivery systems, and related methods of implantation that are conducive to percutaneous delivery for replacing a deficient, previously implanted bioprosthetic heart valve.

SUMMARY

The replacement valves of the invention are configured to provide complimentary features that promote physical docking or connection of the replacement heart valve to a previously implanted prosthetic heart valve, such as the aortic valve, mitral valve, pulmonic valve, and tricuspid valve. In some embodiments, the replacement heart valve and related methods of implantation of the invention utilize a previously implanted prosthetic heart valve as a platform to facilitate mounting relative to a native heart valve. Thus, the replacement heart valves of the invention are highly amenable to percutaneous delivery, although delivery of the heart valves using an apical approach (either with or without cardiopulmonary bypass) is also contemplated. Further, in cases where a previously implanted prosthetic heart valve is being functionally replaced, the deficient prosthetic heart valve need not be physically removed from the patient. Thus, the prosthetic heart valve and related method of implantation of the present invention can be used at any point during the "useful life" of a conventional prosthetic heart valve. Further, the methodology associated with the present invention can be repeated multiple times, such that several prosthetic heart valves of the present invention can be mounted on top of or within one another, if necessary or desired.

The replacement heart valves of the invention each include a stent to which a valve structure is attached. The stents of the invention include a wide variety of structures and features that can be used alone or in combination with features of other stents of the invention. In particular, these stents provide a number of different docking and/or anchoring structures that cooperate with the structure of a previously implanted prosthetic heart valve, and are conducive to percutaneous delivery thereof. Many of the structures are thus compressible to a relatively small diameter for percutaneous delivery to the heart of the patient, and then are expandable either via removal of external compressive forces (e.g., self-expanding stents), or through application of an outward radial force (e.g., balloon expandable stents). In a further alternative, some portions of a stent may be self-expanding while other portions of the same stent are expandable through application of an externally applied force.

Insertion or implantation of the replacement heart valves of the invention can be accomplished using delivery systems that can maintain the stent structures in their compressed state during their insertion and allow or cause all or specific features of the stent structures to expand once they are in their desired location. In addition, some stents of the invention can further include features that allow them to be retrieved for removal or relocation thereof after they have been deployed from the stent delivery systems. The methods may include implantation of the stent structures using either an antegrade or retrograde approach. Further, in many of the delivery approaches of the invention, the stent structure is rotatable in vivo to allow the stent structure to be positioned in a desired orientation.

BRIEF DESCRIPTION OF THE DRAWINGS

The present invention will be further explained with reference to the appended Figures, wherein like structure is referred to by like numerals throughout the several views, and wherein:

FIGS. 7-10 are sequential perspective views of the implantation of a self-expanding stent in a prosthetic heart valve, utilizing a retrograde approach of implantation;

FIG. 16 is a perspective view of another exemplary embodiment of a stent of a replacement heart valve of the invention, with the stent in a partially compressed state;

FIG. 17 is a perspective view of the stent of FIG. 16 positioned within a prosthetic heart valve;

FIG. 18 is a side view of the stent and heart valve of FIG. 17;

FIG. 19 is a top view of the stent of FIG. 16 as positioned relative to the outflow end of a prosthetic heart valve, with the stent in its expanded state;

FIG. 20 is a bottom view of the stent of FIG. 16 as positioned relative to the inflow end of a prosthetic heart valve, with the stent in its expanded state;

FIG. 21 is a perspective view of the stent of FIG. 16 in its expanded state;

FIG. 22 is a perspective view of the stent of FIGS. 16-21 as positioned relative to a prosthetic heart valve;

FIG. 25 is a perspective view of another exemplary embodiment of a stent of a replacement valve of the invention, positioned within a prosthetic heart valve;

FIG. 26 is a top view of the stent of FIG. 25 as positioned relative to the outflow end of a prosthetic heart valve;

FIG. 27 is a bottom view of the stent of FIG. 25 as positioned relative to the inflow end of a prosthetic heart valve;

FIG. 28 is a perspective view of the stent of FIG. 25;

FIG. 29 is a side view of the stent of FIG. 28 positioned relative to a prosthetic heart valve;

FIG. 30 is a perspective view of another exemplary embodiment of a stent of a replacement valve of the invention positioned within a prosthetic heart valve;

FIG. 31 is a top view of the stent of FIG. 30, as positioned relative to the outflow end of a prosthetic heart valve;

FIG. 32 is a bottom view of the stent of FIG. 30, as positioned relative to the inflow end of a prosthetic heart valve;

FIG. 33 is a perspective view of the stent of FIG. 30;

FIG. 34 is a side view of the stent positioned within a prosthetic heart valve of FIG. 30;

FIG. 35 is a perspective view of another exemplary embodiment of a stent of a replacement valve of the invention positioned within a prosthetic heart valve, with the stent in its partially compressed state;

FIG. 36 is a perspective view of the stent of FIG. 35 in its partially compressed state;

FIG. 37 is a side view of the stent positioned within a prosthetic heart valve of FIG. 35;

FIG. 38 is a perspective view of the stent of FIGS. 35-37 positioned within a prosthetic heart valve, with the stent in its expanded state;

FIG. 39 is a perspective view of the stent of FIG. 38;

FIG. 40 is a top view of the stent of FIG. 38, as positioned relative to the outflow end of a prosthetic heart valve;

FIG. 41 is a bottom view of the stent of FIG. 38, as positioned relative to the inflow end of a prosthetic heart valve;

DETAILED DESCRIPTION

Figure 1:
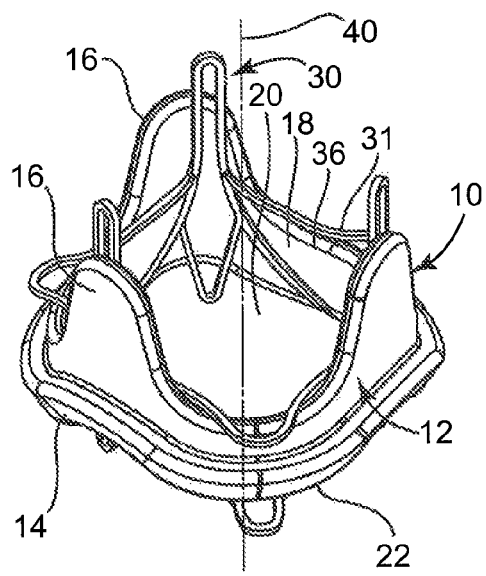
FIG. 1 is a perspective view of a prosthetic heart valve with a stent of a replacement prosthetic heart valve of the invention positioned therein.

Referring now to the Figures, wherein the components are labeled with like numerals throughout the several Figures, and initially to FIG. 1, a prosthetic heart valve 10 is illustrated with a stent 30 of the invention positioned therein, which will be described in further detail below. However, referring specifically to the prosthetic heart valve 10, this valve 10 is a typical configuration of a valve that can be implanted within the heart of a patient, such as by suturing or otherwise securing the valve 10 into the area of a native heart valve of a patient. The native heart valves referred to herein can be any of the human heart valves (i.e., mitral valve, tricuspid valve, aortic valve, or pulmonary valve), wherein the type and orientation of an implanted (e.g., surgically implanted) prosthetic heart valve 10 will correspond with the particular form, shape, and function of the native heart valve in which it is implanted. Although valve 10 would typically include multiple leaflets attached within its interior area, such leaflets are not shown in many of the illustrated embodiments for clarity purposes.

Valve 10 generally includes a valve structure 12 including a stent ring 14 from which three stent posts or commissure posts 16 extend. All or a portion of the valve structure 12, including the stent ring 14 and stent posts 16, can be covered by a flexible covering 18, which may be a tissue, polymer, fabric, cloth material, or the like to which leaflets (not shown) of the heart valve 10 are attached, such as by sewing. Further, as is known in the art, the internal structure of each of the stent posts 16 can be formed of a stiff but somewhat resiliently bendable material. This construction allows the stent posts 16 to be moved from the orientation shown in FIG. 1 to a deflected orientation by the application of an external force. Once this external force is removed or reduced, the stent posts 16 can then move back toward the orientation shown in FIG. 1.

The valve structure 12 is generally tubular in shape, defining an internal area 20 (referenced generally) that extends from an inflow end 22 to an outflow end 24. The internal area 20 is essentially surrounded by the valve structure 12, and the leaflets attached within the valve structure 12 selectively allow for fluid flow into or out of the lumen of the natural heart valve in which it is implanted. That is, the internal area 20 is alternatively open and closed to the lumen of the natural heart valve in which it is inserted via movement of leaflets. In some patients, the prosthetic heart valve 10 will have previously been implanted in a patient using typical surgical techniques, whereby the stent ring 14 is sewn or attached to the annulus or valvular rim of the native heart valve. Alternatively, the prosthetic valve could have been previously placed in the patient using minimally invasive techniques for holding the valve in place, such as U-clips, for example, or a wide variety of other techniques and features used for minimally invasive and/or percutaneous implantation of the initial prosthetic heart valve.

The prosthetic heart valves (e.g., heart valve 10) used in accordance with the devices and methods of the invention may include a wide variety of different configurations, such as a prosthetic heart valve that has tissue leaflets, or a synthetic heart valve that has polymeric leaflets. In this way, the prosthetic heart valves can be specifically configured for replacing any heart valve. That is, while much of the description herein refers to replacement of aortic valves, the stents (and their associated leaflets) of the invention can also generally be used for replacement of tricuspid valves, for use as a venous valve, or to replace a failed bioprosthesis, such as in the area of an aortic valve or mitral valve, for example. The replacement prosthetic heart valves of the present invention can be employed to functionally replace stentless prosthetic heart valves as well.

The replacement prosthetic heart valves of the present invention can facilitate an implantation technique whereby a replacement prosthetic heart valve is situated or placed relative to a previously implanted prosthetic heart valve, which may be configured as the heart valve 10 shown and described herein. This would become a desirable procedure in cases where it is determined that a previously implanted prosthetic heart valve is functionally deficient due to one or more of a variety of factors, such as stenosis, valve failure, inflammation, native valve insufficiency, etc. Regardless of the cause of the deficiency, rather than removing the previously implanted prosthetic heart valve and implanting a second, similarly formed prosthetic heart valve via relatively complicated and invasive open heart surgical techniques, the methods and devices of the present invention leave the deficient previously implanted prosthetic heart valve in place, and deploy the new prosthetic heart valve so that it functionally replaces the previously implanted prosthetic heart valve. Prior to implanting the new prosthetic valve, the leaflets of the previously implanted and deficient prosthetic heart valve can either be removed using a variety of techniques such as cutters, lasers, and the like, or the leaflets may instead be left in place within the deficient valve, where they will likely be pushed toward the walls of the vessel upon implantation of the new valve.

One embodiment of a stent 30, which can be used as a component of a prosthetic heart valve in accordance with the present invention, is shown in FIGS. 1-4. Stent 30 includes a support structure 31 comprising a number of strut or wire portions arranged relative to each other to provide secure coupling between the stent 30 and a prosthetic heart valve 10 in which it is located. In addition, stent 30 provides a semi-rigid frame for the leaflets of the replacement heart valve, which will be attached in some way within the interior portion of stent 30. For ease and clarity of illustration, the leaflets associated with the replacement heart valves of the invention are not shown in the embodiments of the stents of the invention illustrated herein. Details of several configurations of the stents of the invention are described below; however, in general terms, the stents of the invention are generally a series of wires arranged into a tubular support structure, and leaflets can be secured to the interior of the support structure. The leaflets can be formed from a variety of materials, such as autologous tissue, xenograph material, synthetics, or the like, as known in the art. The leaflets may be provided as a homogenous, biological valve structure, such as a porcine, bovine, or equine valve. Alternatively, the leaflets can be provided independent of one another (e.g., bovine or equine pericardial leaflets) and subsequently assembled and attached to a stent support structure. The support structures shown and described relative to the Figures are generally configured to accommodate three leaflets and replace a heart valve (e.g., heart valve 10) that has three commissure posts that accommodate a three-leaflet structure. However, the replacement prosthetic heart valves of the invention can incorporate more or less than three leaflets.

In more general terms, the combination of a support structure with one or more leaflets can assume a variety of other configurations that differ from those shown and described, including any known prosthetic heart valve design. In one embodiment, a stent support structure with leaflets can be any known expandable prosthetic heart valve configuration, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "*Percutaneous Insertion of the Pulmonary Valve*", Pediatric Cardiology, 2002; 39:1664-1669; Andersen H R, et al., "*Transluminal Implantation of Artificial Heart Valves*", EUR Heart J., 1992; 13:704-708; Andersen, H. R., et al., "*Transluminal Catheter Implantation of New Expandable Artificial Cardiac Valve*", EUR Heart J., 1990, 11: (Suppl) 224a; Hilbert S. L., "*Evaluation of Explanted Polyurethane Trileaflet Cardiac Valve Prosthesis*", J Thorac Cardiovascular Surgery, 1989; 94:419-29; Block P C, "*Clinical and Hemodyamic Follow-Up After Percutaneous Aortic Valvuloplasty in the Elderly*", The American Journal of Cardiology, Vol. 62, Oct. 1, 1998; Boudjemline, Y., "*Steps Toward Percutaneous Aortic Valve Replacement*", Circulation, 2002; 105:775-558; Bonhoeffer, P., "*Transcatheter Implantation of a Bovine Valve in Pulmonary Position, a Lamb Study*", Circulation, 2000:102:813-816; Boudjemline, Y., "*Percutaneous Implantation of a Valve in the Descending Aorta In Lambs*", EUR Heart J. 2002; 23:1045-1049; and Kulkinski, D., "*Future Horizons in Surgical Aortic Valve Replacement: Lessons Learned During the Early Stages of Developing a Transluminal Implantation Technique*", ASAIO J, 2004; 50:364-68).

Referring again to FIGS. 1-4, the stent 30 comprises a support structure 31 that is made up of a number of struts or wire segments arranged to provide desired docking or engagement features. As will be described in further detail below, the support structure 31 may either be made up of a number of individual struts or wire segments arranged and secured to each other, or the support structure 31 may instead be formed from a single piece of material (e.g., a tube of material that is machined to provide the structure shown). With particular regard to FIG. 1, stent 30 is positioned within a heart valve 10, which typically would have been previously implanted in a patient. Stent 30 comprises a support structure 31 having multiple upper vertical members 32 spaced apart from each other around the perimeter of the support structure 31, and a corresponding number of lower vertical members 34. Both the upper and lower vertical members 32, 34 extend in a direction that is generally parallel to a longitudinal axis 40 of the support structure 31, and help to define the generally cylindrical shape of the support structure 31. Upper vertical members 32 extend generally toward the outflow end 24 of the valve structure 12, and the lower vertical members 34 extend in a direction that is generally opposite to the direction of the upper vertical members 32, which is toward the inflow end 22 of the valve structure 12.

Each of these upper and lower vertical members 32, 34 are preferably spaced from adjacent upper and lower vertical members 32, 34, respectively, by a distance that is similar or identical to the distance that the stent posts (e.g., stent posts 16) are spaced from each other in a corresponding implanted heart valve (e.g., heart valve 10). Thus, both the number of upper vertical members 32 and the number of lower vertical members 34 are typically the same as the number of stent posts. However, it is possible that the number of upper and lower vertical members 32, 34 are not the same as each other and/or not the same as the number of stent posts.

The upper vertical members 32 are designed to have a height that allows them to have a desired amount of contact with a corresponding stent post. The upper vertical members 32 may extend at least slightly beyond the tops of the stent posts, or may be at least slightly shorter than the stent posts. The lower vertical members 34 may also have any length that allows them to have a desired amount of contact with their corresponding stent posts 16 and other portions of the stent structure 12 with which they come into contact. Again, the lower vertical members 34 may extend at least slightly below the bottom of the stent structure (i.e., stent ring 14 of FIG. 1), or may be at least slightly shorter so that they do not extend below any portion of the stent structure. The selection of the length of these upper and lower vertical members 32, 34 can vary widely, depending on the configuration of the valve structure and the amount of contact desired between the support structure 31 and the interior portion of the stent or valve structure. In any case, the height of upper and lower vertical members 32, 34 should be adequate to provide sufficient contact between the support structure 31 and the corresponding heart valve in which it is positioned to keep the stent 30 in place relative to the heart valve. In addition, the arrangement of upper and lower vertical members 32, 34 should provide sufficient structural integrity to the support structure 31 so that it is resistant to deformation or other changes that impact its effectiveness as a stent structure.

The upper and lower vertical members 32, 34 may be generally "U" or "V" shaped, as illustrated, with the distance between opposite "legs" or extending portions of the members being chosen to provide desired characteristics to the support structure 31. For example, in FIG. 1, the upper vertical members 32 are preferably narrow enough that they will not unintentionally engage with the top edge of corresponding stent posts 16, but are preferably wide enough that they provide adequate contact with the interior portion of the stent posts 16 to help keep the stent 30 in place. In other words, the distance between opposite legs of the "U" or "V" shaped structure is preferably not so large that the members 32 can latch onto the stent posts 16, but is preferably large enough to provide contact between the members 32 and some portion of the interior surface of the stent posts 16. This "U" or "V" shaped structure of these members 32, 34 is particularly adaptable to the configuration where the support structure 31 is essentially a continuous wire structure; however, if the support structure is configured in another manner (e.g., with separate components that are not wire-like), each of the members 32, 34 may essentially consist of a single, relatively solid extending structure, for example. These structures may be arranged and connected relative to each other in a similar configuration to that described relative to a wire structure.

As shown in FIG. 1, heart valve 10 includes three stent posts 16 that are spaced generally at an equal distance from each other around the perimeter of the valve 10 (i.e., approximately 120 degrees apart). These stent posts 16 will generally correspond with the commissures of leaflets of the valve (not shown). It is understood, however, that the stent posts 16 may instead be unevenly spaced from each other. In one example of such an embodiment, first and second stent posts 16 may be spaced from each other by approximately 120 degrees, second and third stent posts 16 may be spaced from each other by approximately 115 degrees, so that first and third stent posts 16 would be spaced from each other by approximately 125 degrees. Other arrangements that vary slightly or substantially from this arrangement may alternatively be used; particularly in cases where more or less than two stent posts 16 are used. One example of such an arrangement would be in the case of a two-leaflet valve (e.g., the mitral valve), which would only include two stent posts arranged at approximately 180 degrees from each other and a corresponding arrangement for its support structure 31.

Figure 4:
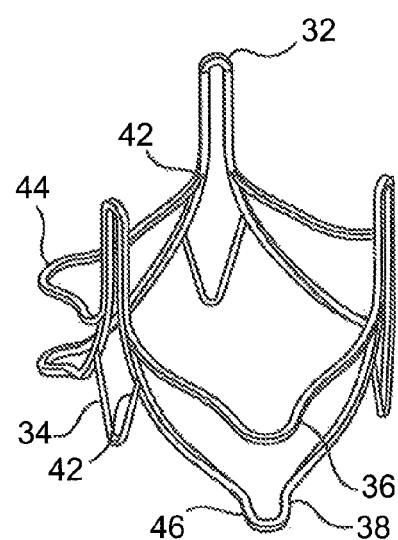
FIG. 4 is a perspective view of the stent of FIG. 1 as it can be used as a component of a replacement prosthetic heart valve.

Support structure 31 further includes multiple upper flange or petal portions 36, each of which is located generally between two adjacent upper vertical members 32, and multiple lower flange or petal portions 38, each of which is located generally between two adjacent lower vertical members 34. As is best shown in FIG. 4, the upper and lower flange portions 36, 38 both extend from a common area 42 of the support structure 31, which generally corresponds with the area where the upper and lower vertical members 32, 34 meet. However, the upper and lower flange portions 36, 38 may instead extend from the vertical members 32, 34 at locations that are spaced further from each other. In any case, the upper and lower flange portions 36, 38 are provided for engagement with the stent or valve structure 12 on generally opposite edges (i.e., top and bottom edges) of the stent ring 14 when positioned within a heart valve 10. That is, the upper flange portions 36 will be positioned in the area between adjacent stent posts 16 on the outflow end 24 of the valve structure 12, and the lower flange portions 38 will be positioned generally below the upper flange portions 36, but on the opposite side of the valve structure 12 (i.e., along the bottom edge of the stent ring 14 on the inflow end 22 of the valve structure 12).

Orientation and positioning of the stents of the invention may be accomplished either by self-orientation of the stents (such as by interference between features of the stent and a previously implanted stent or valve structure) or by manual orientation of the stent to align its features with anatomical or previous bioprosthetic features, such as can be accomplished using fluoroscopic visualization techniques, for example. For example, when aligning the stents of the invention with a previously implanted bioprosthetic valve, features of the stents can align with the stent rail and/or commissures of the valve. It is desirable that the stents be locked in place both rotationally and axially.

Referring again to FIGS. 1-4, the length and shape of each of these upper and lower flange portions 36, 38 can be the same or different from each other within a single support structure 31, as desired. For example, if the stent posts of a corresponding heart valve are spaced evenly from each other, it may be desirable for the flange portions to be identically spaced, although they may be different from each other in size and/or shape. In any case, it is desirable for the upper and lower flange portions 36, 38 to extend at least slightly beyond the outer perimeter of the valve structure 12 when the stent is deployed in order to insure adequate contact between the valve structure 12 and the stent 30. However, the amount of extension of the upper and lower flanges beyond the outer surface of the valve structure 12 should not be so large that it interferes with any surrounding structure of the heart, as will be discussed in further detail below.

The upper and lower flange portions 36, 38 may be generally "U" or "V" shaped, as illustrated, although the distance between opposite "legs" or extending portions of the members will generally be larger than the distance between the legs of the upper and lower vertical members 32, 34 within the same stent 30, particularly when the stent 30 is in its expanded state. Each upper flange portion 36 includes a distal tip 44 and each lower flange member 38 includes a distal tip 46. The tips 44, 46 may have a tighter curvature than the rest of their respective flange portions 36, 38, if desired. In any case, the tips 44, 46 preferably will contact the upper and lower edges of a stent ring of a heart valve when implanted therein. The tips 44, 46 may also serve as interfaces or connecting portions with a corresponding delivery system, as will be explained in further detail below.

The lower flange portions 38 are configured to engage with the lower surface of a sewing ring 14 of a previously implanted prosthetic heart valve (e.g., heart valve 10) when the stent 30 is in its expanded condition. Alternatively, the lower flange portions 38 can be configured to engage other structure(s) of the previously implanted prosthetic heart valve. Referring to FIG. 1, in order to engage with a previously implanted heart valve, one exemplary embodiment of a lower flange portion 38 includes a wire structure that extends generally from a common area 42 on one upper vertical member 32 toward the tip 46 of the flange portion 38, then toward another common area 42 on an adjacent upper vertical member 32. The curvature or contours of each flange portion 38 can be designed so that it closely matches the shape of the stent or valve structure 12 in which it will be implanted, such as at its inflow end 22. That is, there is preferably minimal to no gap between the flange 38 and the interior surface of the valve structure 12.

Figure 3:
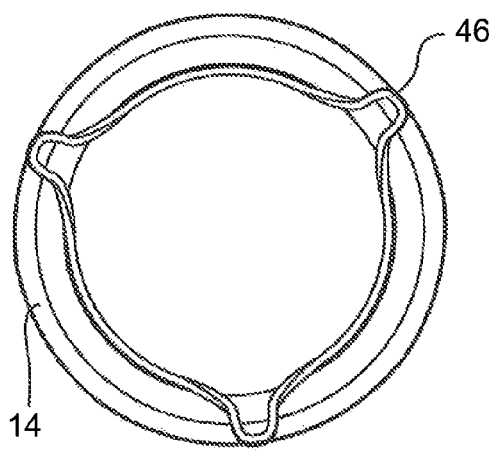
FIG. 3 is a bottom view of the stent of FIG. 1 as positioned relative to the inflow end of a prosthetic heart valve.

As shown in FIG. 3, each of the tips 46 of the flange portions 38 are positioned approximately 120 degrees from each other around the periphery of the sewing ring 14, although they can be spaced differently from each other, depending on the locations of the stent posts of the heart valve. When the stent 30 is in an expanded condition, the lower flange portions 38 are preferably biased toward the sewing ring 14 to keep the flange portion 38 in place relative to the heart valve 10.

Figure 2:
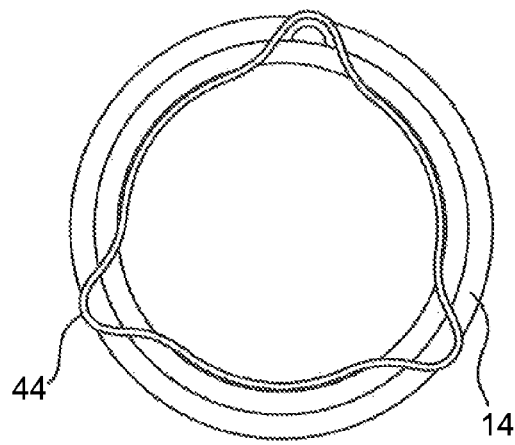
FIG. 2 is a top view of the stent of FIG. 1 as positioned relative to the outflow end of a prosthetic heart valve.

The upper flange portions 36 are configured to engage with the spaces between stent posts 16 of a previously implanted heart valve (e.g., heart valve 10) when the stent 30 is in its expanded condition. Alternatively, the upper flange portions 36 can be configured to engage other structure(s) of the previously implanted prosthetic heart valve. Referring to FIG. 1, in order to engage with a previously implanted heart valve, one exemplary embodiment of an upper flange portion 36 includes a wire structure that extends generally from a common area 42 on one upper vertical member 32 toward the tip 44 of the flange portion 36, then toward another common area 42 on an adjacent vertical member 32. The curvature or contours of each flange portion 36 can be designed to closely match the shape of the stent or valve structure 12 in which it will be implanted. As shown in FIG. 2, each of the tips 44 of the flange portions 36 are positioned approximately 120 degrees from each other around the periphery of the sewing ring 14, although they can be spaced differently from each other, depending on the locations of the stent posts of the heart valve. In any case, the tip 44 of flange portion 36 will preferably fit between adjacent stent posts 16 in order to help physically dock or connect the stent 30 to the previously implanted heart valve 10. When the stent 30 is in an expanded condition, the upper flange portions 36 are preferably biased toward the sewing ring 14 (and preferably toward a corresponding lower flange portion 38) to keep each flange portion 36 in place relative to the heart valve 10.

The support structure 31 of the stent 30 is, in one embodiment, a wire stent capable of transitioning from a collapsed state to an expanded state, where a number of individual wires comprising the support structure 31 are formed of a metal or other material. These wires are arranged in such a way that a support structure 31 is provided that allows for folding or compressing to a contracted state in which its internal diameter is at least somewhat smaller than its internal diameter in an expanded state. In its contracted state, such a support structure 31 with attached valves can be mounted relative to a delivery device, such as a balloon catheter, for example. The support structure 31 is configured so that it can be changed to its expanded state when desired, such as by the expansion of a balloon catheter. The delivery systems used for such replacement heart valve can optionally be provided with degrees of rotational and axial orientation capabilities in order to properly position the new heart valve within the previously implanted heart valve.

The wires of the support structure 31 can alternatively be formed from a shape memory material such as a nickel titanium alloy (e.g., Nitinol). With this configuration, the support structure 31 is self-expandable from a contracted state to an expanded state, such as by the application of heat, energy, and the like, or by the removal of external forces (e.g., compressive forces). In addition, the support structure 31 of this embodiment may be laser cut from a single piece of material or may be assembled from a number of different components. For these types of stent structures, one example of a delivery system that can be used includes a catheter with a retractable sheath that covers a compressed stent (thereby providing external compressive forces on the stent) until it is to be deployed, at which point the sheath can be retracted to allow the stent to expand.

The support structure 31 can include features not specifically described or shown instead of, or in addition to, the various coupling structures and methods described herein. For example, the support structure 31 can have a non-expandable design, but can instead be sized and shaped to nest within a previously implanted heart valve (not shown) in a manner that presses features of the previously implanted heart valve (e.g., leaflets) outwardly relative to the native conduit.

The height and diameter of the stent 30 in its expanded state is preferably chosen and/or designed for use with a previously implanted prosthetic heart valve having a particular size and shape. Thus, the stent 30 can assume a variety of different longitudinal heights and/or diameters. In one embodiment, for example, the support structure 31 has a height in its expanded state that is slightly greater than a height of the previously implanted prosthetic heart valve, and/or has a free-standing outer diameter that is greater than an inner diameter of the previously implanted prosthetic heart valve. With this embodiment, upon transitioning toward the expanded state, the support structure 31 (including the vertical members 32, 34) presses against an inner diameter of the previously implanted prosthetic heart valve. The overall shape of the support structure 31 is cylindrical in many cases; however, other shapes are also contemplated, such as elliptical, oval, or the like. For example, portions of the support structure 31 can define an enlarged diameter as compared to other portions. Further, depending upon the previously implanted heart valve being functionally replaced, the support structure 31 can be less uniform along a height thereof.

Figure 6:
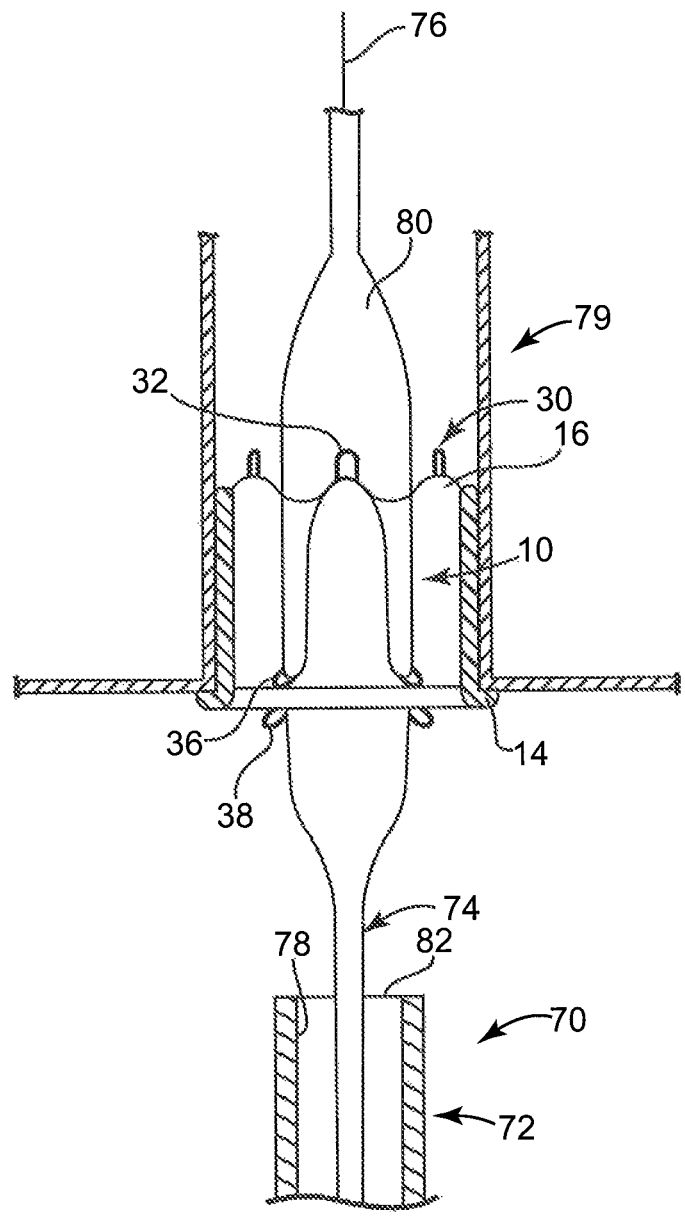
FIG. 6 is a side, partial cross-sectional view of one embodiment of a delivery system of the invention for implanting a balloon-expandable stent of a replacement prosthetic heart valve.
Figure 12:
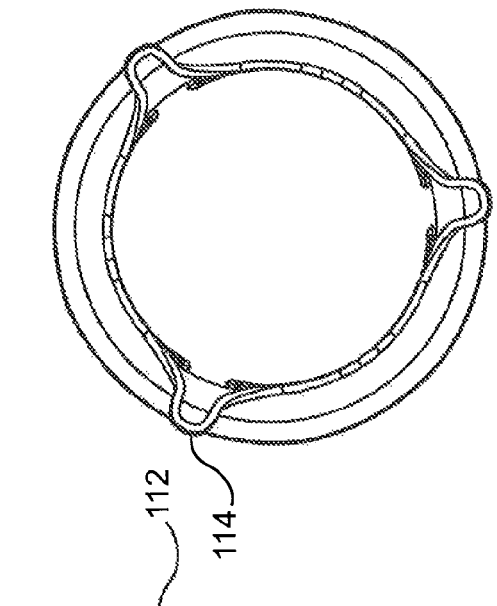
FIG. 12 is a top view of the stent of FIG. 11 as positioned relative to the outflow end of a prosthetic heart valve.
Figure 14:
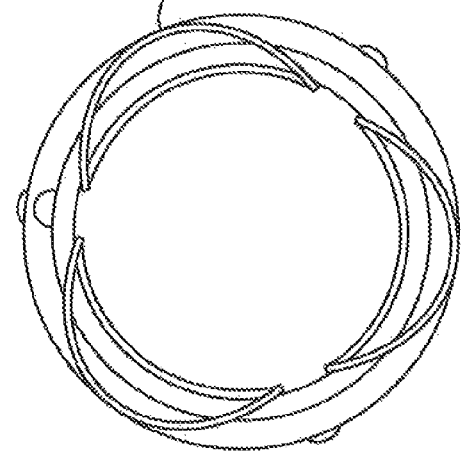
FIG. 14 is a perspective view of the stent of FIG. 11 as it can be used as a component of a replacement prosthetic heart valve.
Figure 11:
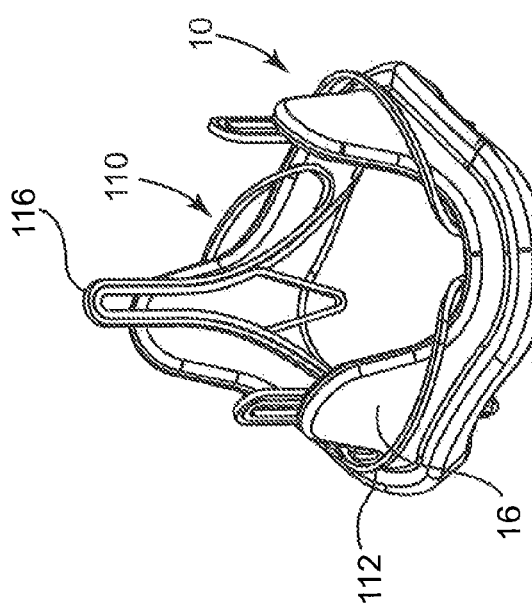
FIG. 11 is a perspective view of a prosthetic heart valve with another exemplary embodiment of a stent of a replacement prosthetic heart valve of the invention positioned therein.
Figure 13:
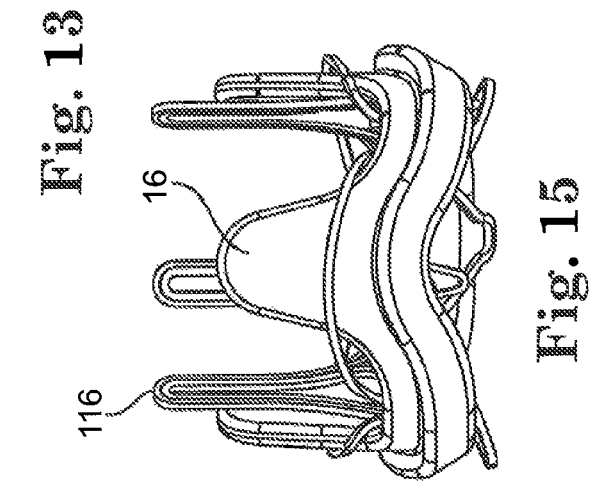
FIG. 13 is a bottom view of the stent of FIG. 11 as positioned relative to the inflow end of a prosthetic heart valve.
Figure 15:
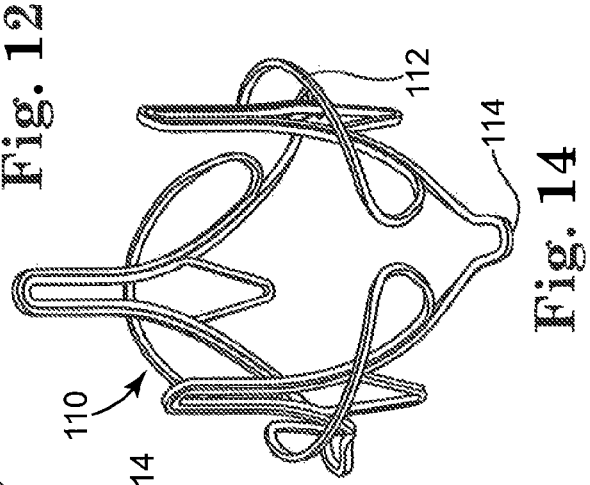
FIG. 15 is a side view of the stent and prosthetic heart valve of FIG. 11.

One method of delivering the stent 30 to the location of a previously implanted heart valve (e.g., heart valve 10) is performed percutaneously, as represented in simplified form in FIG. 6. In general terms for this exemplary delivery system, a transcatheter assembly 70 is provided, including a delivery catheter 72, a balloon catheter 74, and a guide wire 76. The delivery catheter 72 is of a type known in the art, and defines a lumen 78 within which the balloon catheter 74 is received. The balloon catheter 74, in turn, defines a lumen (not shown) within which the guide wire 76 is slidably disposed. Further, the balloon catheter 74 includes a balloon 80 that is fluidly connected to an inflation source (not shown). It is noted that if the stent being implanted is a self-expanding type of stent, the balloon would not be needed and a sheath or other restraining means would instead be used for maintaining the stent in its compressed state until deployment of the stent. In any case, in this embodiment, the transcatheter assembly 70 is appropriately sized for a desired percutaneous approach to the prosthetic heart valve 10 that was previously implanted in a native heart valve 79. For example, the transcatheter assembly 70 can be sized for delivery to the heart valve 10 via an opening at a carotid artery, a jugular vein, a sub-clavian vein, femoral artery or vein, or the like. Essentially, any percutaneous intercostals penetration can be made to facilitate use of the transcatheter assembly 70.

Prior to delivery, the stent 30 is mounted over the balloon 80 in a contracted state to be as small as possible without causing permanent deformation of the stent structure. As compared to the expanded state, the support structure 31 is compressed onto itself and the balloon 80, thus defining a decreased inner diameter as compared to an inner diameter in the expanded state. Further, the vertical members 32, 34 and flange portions 36, 38 are compressed toward the longitudinal axis 40 when in the contracted state. While this description is related to the delivery of a balloon-expandable stent, the same basic procedures can also be applicable to a self-expanding stent, where the delivery system would not include a balloon, but would preferably include a sheath or some other type of configuration for maintaining the stent in its compressed condition until its deployment.

With the stent 30 mounted to the balloon 80, the transcatheter assembly 70 is delivered through a percutaneous opening (not shown) in the patient via the delivery catheter 72. The previously implanted heart valve 10 is located by inserting the guide wire 76 into the patient, which guide wire 76 extends from a distal end 82 of the delivery catheter 72, with the balloon catheter 74 otherwise retracted within the delivery catheter 72. Once the previously implanted heart valve 10 has been located, the balloon catheter 74 is advanced distally from the delivery catheter 72 along the guide wire 76, with the balloon 80 and stent 30 positioned relative to the previously implanted heart valve 10. More particularly, the balloon 80 and stent 30 are positioned within the internal region of the previously implanted prosthetic heart valve 10, with the lower flange portions 38 positioned adjacent the sewing ring 14 of the heart valve 10, and the upper flange portions 36 are positioned adjacent the outflow end 24 of the previously implanted prosthetic heart valve 10.

In an alternative embodiment, the stent 30 is delivered to the previously implanted prosthetic heart valve 10 via a minimally invasive surgical incision (i.e., non-percutaneously). In another alternative embodiment, the stent 30 is delivered via open heart/chest surgery. Regardless, with the stent 30 in the contracted state, the support structure 31 can readily move within the internal area 20 of the previously implanted prosthetic heart valve 10, and the vertical members 32, 34 and flange portions 36, 38, which are otherwise retracted or compressed, do not unintentionally contact or engage portions of the previously implanted prosthetic heart valve 10. In one embodiment, the stent 30 includes a radiopaque, echogenic, or MRI visible material to facilitate visual confirmation of proper placement of the stent 30 relative to the previously implanted prosthetic heart valve 10. Alternatively, other known surgical visual aids can be incorporated into the stent 30.

The techniques described above relative to placement of the stent 30 within the heart can be used both to monitor and correct the placement of the stent 30 in a longitudinal direction relative to the length of the anatomical structure in which it is positioned and also to monitor and correct the orientation of the stent 30 relative to the stent posts 16 of the previously implanted heart valve 10. In particular, it is desirable for the stent 30 to be positioned so that each of the upper flange portions 36 are between two adjacent stent posts 16 when they are expanded outwardly.

Once the stent 30 is properly positioned, the balloon catheter 74 is operated to inflate the balloon 80, thus transitioning the stent 30 to the expanded state shown in FIG. 1. Alternatively, if the support structure 31 is formed of a shape memory material, the stent can be allowed to self-expand to the expanded state of FIG. 1. Thus, a self-expanding stent structure can be percutaneously delivered by an appropriate catheter device other than a balloon catheter, as will be described in further detail below. In either case, the support structure 31 expands within the internal region 20 of the previously implanted heart valve 10, radially pressing against the valve structure 12. Because the previously implanted prosthetic heart valve 10 would have included leaflets (not shown), radial expansion of the stent 30 would press against these leaflets, thereby lodging them against the valve structure 12.

Figure 5:
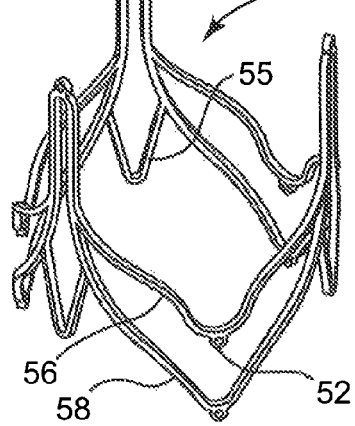
FIG. 5 is a perspective view of another embodiment of a stent of the invention as it can be used as a component of a replacement prosthetic heart valve.

FIG. 5 illustrates an exemplary embodiment of a stent 50 that includes a number of eyelets or apertures 52 that can be used for maintaining the various components of stent 50 in a compressed state when desired. These eyelets 52 would be particularly useful in the case where the stent 50 is a self-expanding stent, since this type of structure needs external forces to keep it in its compressed state. In particular, an eyelet 52 may be located at the end of at least one of the multiple upper vertical members 54 and/or one or more of the upper and lower flange portions 56, 58 and the lower vertical members 55. Each eyelet 52 is preferably sized for accepting an elongated thread-like material, such as suture material or a thin wire, and/or sized for engagement with a hook or other engagement feature of a delivery device. If a thread-like material is used, it can be threaded through at least one of the eyelets 52 in such a way that when the material is pulled tight, the eyelets 52 are pulled toward the central axis of the stent 50. If a wire-like material is used, it may be configured as a metal snare or other configuration that pulls the eyelets 52 toward the central axis of the stent 50. If a delivery device having such engagement features is used, it may be configured in such a way that the engagement features can be moved toward and away from the central axis of the stent, as desired for insertion and deployment of the stent.

Other arrangements of pulling the various portions of a stent toward a central stent axis are also contemplated, which preferably are relatively easy to operate for compression and release of the stent structures. In any case, once the stent structure is compressed to its desired configuration, the feature used to pull the stent into its compressed configuration is capable of being secured or fastened in some way to keep the stent from unintentionally expanding. This same feature can have its operation reversed to allow the various structures of the stent to move toward their expanded state.

FIGS. 7-10 illustrate one exemplary system of delivering a stent of the type illustrated in FIG. 5, for example, into a heart valve 10, which would have previously been implanted in a patient. One feature provided by the delivery system of this embodiment is that a self-expanding stent is retrievable after its initial deployment if it is not positioned correctly in the heart. The stent then could be redeployed into the proper position, using the same or a different delivery system. With particular reference to the Figures, a distal portion of a delivery system 90 is illustrated, which includes a tip portion 92 and a sheath 94. The system further includes a plurality of hooks or engagement features 96 that can engage with eyelets 52 of stent 50, for example. While this delivery system 90 can generally be used for more procedures than the described implantation procedure, the procedure illustrated relative to FIGS. 7-10 is particularly directed to percutaneous delivery of a stent to a previously implanted aortic heart valve via a retrograde approach. For purposes of this description of an implantation method, the exemplary stent 50 of FIG. 5 is used in the implantation description; however, a number of different stent embodiments may utilize these same procedures, such as other stent embodiments described relative to the present invention.

As illustrated in FIG. 7, delivery system 90 is being advanced toward heart valve 10 as such a heart valve would have been previously implanted in a patient. A compressed replacement valve (not shown) is encompassed within sheath 94 for insertion into the patient so that there is no contact between the replacement valve and any portion of the patient's internal anatomy during the insertion process.

FIG. 8 illustrates delivery system 90 as it has been further advanced into heart valve 10, and wherein the sheath 94 has been partially retracted away from the tip 92 to expose the stent 50 that was previously compressed therein. Because the upper flange portions 56 were no longer constrained by the sheath 94, these portions 56 were able to move away from a central member 100 of the delivery system 90 as the sheath 94 was retracted. Further, eyelets 52 that extend from the ends of upper vertical members 54 are each engaged by a hook 96 of the delivery system 90. These hooks 96 can be attached to a mechanism within the interior portion of the sheath 94, for example, or may be attached to some other structure that extends through the sheath 94. In either case, hooks 96 can maintain the upper vertical members 54 in their compressed state until they are disengaged from the hooks 96. That is, the delivery system can control the diameter of the stent inflow structures, the stent outflow structures, or both the stent inflow and outflow structures independently or together. As is also illustrated in FIG. 8, the lower flange portions 58 are held in their compressed state with a snare 98 that engages with eyelets 52 that extend from each of the flange portions 58. Snare 98 is shown as a single, shaped piece of elongated material; however, the lower flange portions 58 may instead be held in their compressed state via an alternative structure or system, such as by a suture, or by a moveable sleeve attached to the delivery system, for example.

As shown in FIG. 9, the delivery system 90 is further advanced into valve 10 until the upper flange portions 56, which are extending radially away from the central member 100 of the delivery system 90, become engaged with the valve structure 12 of the heart valve 10. In particular, each of the upper flange portions 56 are preferably positioned to be in contact with the surface of the stent ring 14 between two adjacent stent posts 16. In order to verify that the flange portions 56 are properly positioned relative to the valve structure 12 (e.g., flange portions 56 are not resting on the top of the stent posts 16), the entire delivery system 90 can be rotated slightly in either direction while pressing downwardly toward the valve structure 12. The system 90 can also be advanced axially to the desired position. In this way, the flange portions 56 can be moved into the area between adjacent stent posts 16 if they are not already in this position.

Once the delivery system 90 and its stent 50 are properly oriented, the snare 98, sheath, or other structure holding the lower flange portions 58 in their compressed state is released or retracted, thereby allowing the lower flange portions 58 to deploy or radially extend, as illustrated in FIG. 10. The lower flange portions 58 can then contact the surface of the stent ring 14 that is opposite the surface that is contacted by the upper flange portions 56. The hooks 96 can then be disengaged from the eyelets 52 of stent 50, such as by further advancing the delivery system 90 into the opening of the valve 10, or by activating a mechanism associated with the hooks 96 that can move the hooks 96 relative to the eyelets 52 until they become disengaged from the eyelets 52. It is noted that the stent is retrievable at any point prior to the hooks 96 being disengaged from the stent 50 with use of the hooks 96 and/or the sheath 94. The upper and lower vertical members 54, 55 are then free to expand radially until they contact the inner surface of the stent or valve structure 12. The upper and lower vertical members 54, 55 preferably are configured so that they will press against the inner surface of the valve structure 12 with sufficient force to provide further anchoring of the stent 50 within the previously implanted heart valve 10.

After the stent 50 is implanted and its various portions are deployed or released from a compressed state to an expanded state, the delivery system 90 can be removed from the patient. The stent 50 will then be in its deployed or expanded state, as is generally illustrated in FIG. 5, or in a similar manner to that illustrated in FIG. 1 relative to a stent 30.

FIGS. 11-15 illustrate another exemplary embodiment of a stent 110 that has a similar structure to the stent 30 of FIG. 1, but further includes at least one stent post engaging structure 112. Relative to the specific embodiment of the stent 110 that is illustrated, this structure also does not include upper flange portions (such as upper flange portions 36 of stent 30), since such portions could be redundant and/or interfere with the specific structure of the structures 112 shown. However, it is contemplated that upper flange portions could also be provided with this embodiment, if they are configured to not interfere with any stent post engagement structures 112. Further, in the embodiment shown in the Figures, three structures 112 are provided to correspond with a like number of stent posts 16 of heart valve 10; however it is contemplated that the stent 110 includes less than three structures 112, even if three stent posts are provided. If less than three structures 112 are provided, it may be desirable to additionally provide at least one upper flange portion to engage with the heart valve 10.

Each stent post engaging structure 112 is configured to partially surround a portion of a stent post 16, thereby providing another way of anchoring the stent 110 in place. These structures 112 can cooperate with one or more lower flange portions 114 to provide anchoring on both the inflow and outflow ends of the previously implanted heart valve 10. The structures 112 can be individual structures that are each secured to upper vertical members 116, or may be formed as a single structure having multiple loops that are secured to the structure of the stent 110. Alternatively, these structures 112 can be integrally formed with the structure of the stent 110. Stent 110 can be a self-expanding stent or may be a balloon-expandable stent structure.

FIGS. 16-22 illustrate another exemplary embodiment of a stent 120 for use with a replacement prosthetic heart valve in accordance with the present invention. Stent 120 includes a number of strut or wire portions arranged relative to each other to provide secure coupling between the stent 120 and a previously-implanted prosthetic heart valve, such as heart valve 10. In addition, stent 120 provides a semi-rigid frame for the leaflets of the replacement heart valve, which will be attached to the interior portion of stent 120, as will be described in further detail below.

Stent 120 includes multiple upper vertical members 122 spaced apart from each other around the perimeter of the stent 120, and a corresponding number of lower vertical members 124. It is understood that the number of upper and lower vertical members can be different from each other, however. Both the upper and lower vertical members 122, 124 extend in a direction that is generally parallel to a longitudinal axis of the stent 120, thereby partially defining the generally cylindrical shape of the stent 120. Upper vertical members 122 extend generally toward the outflow end of the stent structure 12, and the lower vertical members 124 extend in a direction that is generally opposite to the direction of the upper vertical members 122, which is toward the inflow end of the stent structure 12. As with previously described embodiments, the number of upper and lower vertical members 122, 124 may or may not be the same as the number of stent posts of the stent structure 12. In addition, the length of upper and lower vertical members 122, 124 should be adequate to provide sufficient contact between the stent 120 and the stent structure 12 to help keep the stent 120 in place relative to the heart valve 10.

Stent 120 further includes upper and lower flange portions 126, 128, respectively. Flange portions 126, 128 are configured for positioning on opposite sides of a stent ring 14 of stent structure 12 when the stent is in its expanded state. Through the design and manufacturing of the stent 120, the flange portions 126, 128 can be biased toward each other when the stent is in its expanded condition in order to keep the stent 120 positioned properly relative to the stent structure 12.

Stent 120 includes components that can be made of materials that perform differently relative to deployment thereof. In particular, a portion of stent 120 can be expandable from its compressed state via the application of an internal radial force (e.g., inflation of a balloon), while another portion of stent 120 can be self-expandable such that the removal of radial compressive forces will allow that portion of stent 120 to expand without application of additional forces. Alternatively, different portions of the stent 120 can be made of different materials that are both self-expanding, or of different materials that are expandable via the application of an internal radial force. Although the components that comprise these two structures can vary, the stent 120 illustrated in FIGS. 16-22 includes a first component that is expandable through application of a radial force. This component may be made of a material such as stainless steel, for example. The first component includes the upper vertical members 122, lower vertical members 124, and lower flange portions 128, and can include a number of components attached to each other, or can be a single machined piece. This first component is illustrated in its compressed state in FIGS. 16-18 and in its expanded state in FIGS. 21 and 22. The stent 120 further includes a second component that is self-expandable and may be made of a shape memory material such as a nickel titanium alloy (e.g., Nitinol). This second component includes the upper flange portions 126 and also a second lower vertical member 130 that can at least roughly duplicate the shape of the lower vertical member 124 of the first component.

When this stent 120 is implanted into a patient, a sheath or other mechanism will be holding the self-expandable portions of the stent in a compressed state until such a mechanism is retracted or removed, thereby allowing the upper flange portions 126 to extend radially from the stent structure, as is illustrated in FIG. 17. These upper flange portions 126 are preferably positionable between adjacent stent posts of a previously implanted heart valve for proper orientation of the stent 120. Because the first component is not made from a self-expandable material, the first component of stent 120 will remain in its compressed state, as shown in FIG. 17, until it is expanded radially, such as via expansion by a balloon catheter that is positioned in its central opening. When fully inflated, such a balloon will be constrained by the stent structure 12 along a portion of its length, but portions of the balloon that are above and below the stent structure 12 can be allowed to expand further so that the balloon takes on an "hourglass" type of shape, thereby pressing the lower flange portions 128 outward and under the stent ring 14, as illustrated in FIG. 22. These lower flange portions 128 can thereby help to anchor the stent 120 relative to the heart valve in which it is positioned. Thus, FIGS. 21 and 22 illustrate the stent 120 in its expanded state, where the upper and lower flange portions 126, 128 are positioned on opposite sides of stent ring 14, and where the vertical members 122, 124, 130 are positioned adjacent to the internal portion of stent structure 12.

Figure 23:
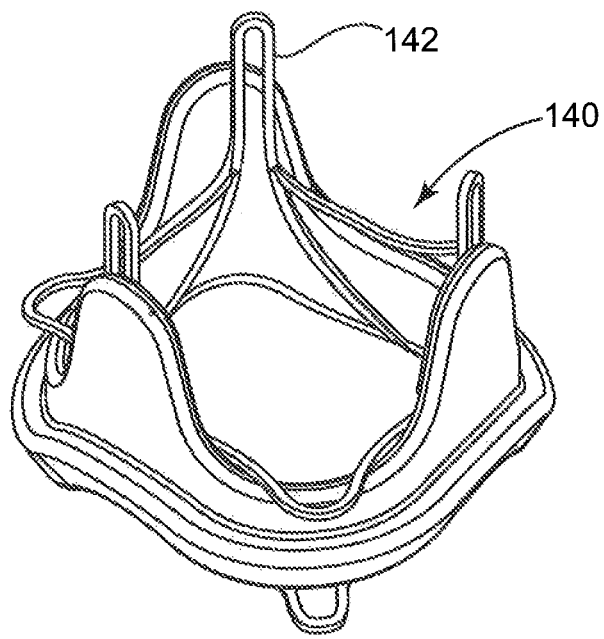
FIG. 23 is a perspective view of another exemplary embodiment of a stent of a replacement valve of the invention, positioned within a prosthetic heart valve.
Figure 24:
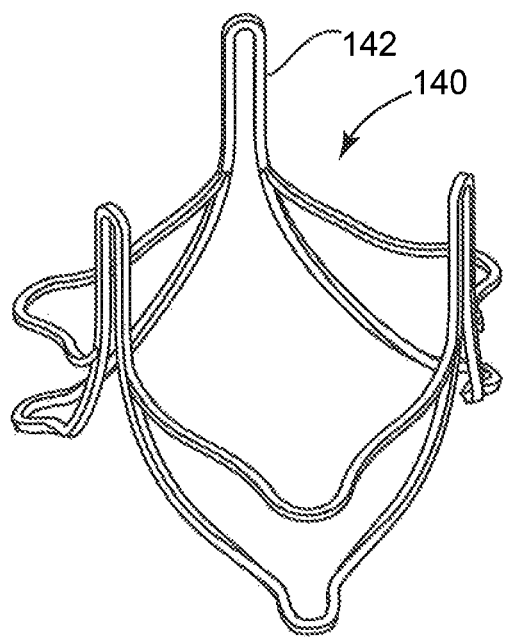
FIG. 24 is a perspective view of the stent of FIG. 23.
Figure 45:
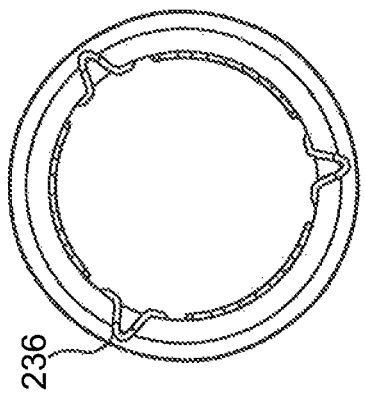
FIG. 45 is a bottom view of the stent of FIG. 42, as positioned relative to the inflow end of a prosthetic heart valve.
Figure 43:
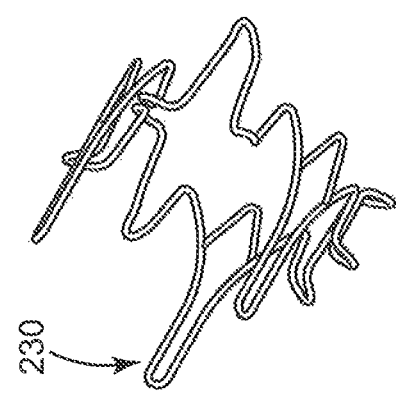
FIG. 43 is a perspective view of the stent of FIG. 42.
Figure 44:
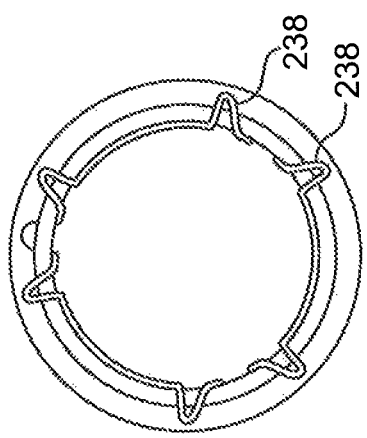
FIG. 44 is a top view of the stent of FIG. 42, as positioned relative to the outflow end of a prosthetic heart valve.
Figure 42:
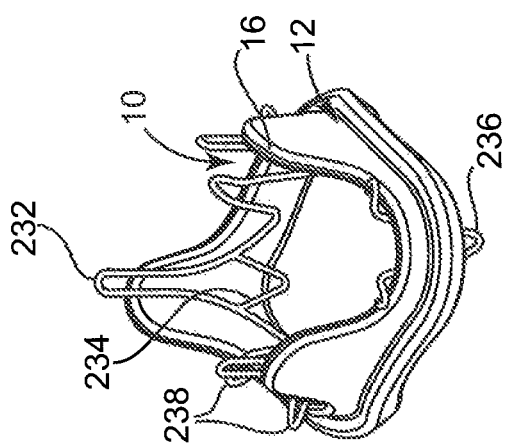
FIG. 42 is a perspective view of another exemplary embodiment of a stent of a replacement valve of the invention positioned within a prosthetic heart valve.
Figure 46:
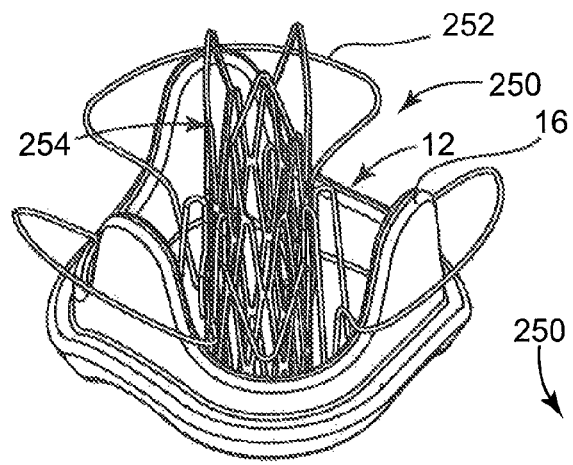
FIG. 46 is a perspective view of another exemplary embodiment of a stent of a replacement valve positioned within a prosthetic heart valve, with the stent in its partially compressed state.
Figure 47:
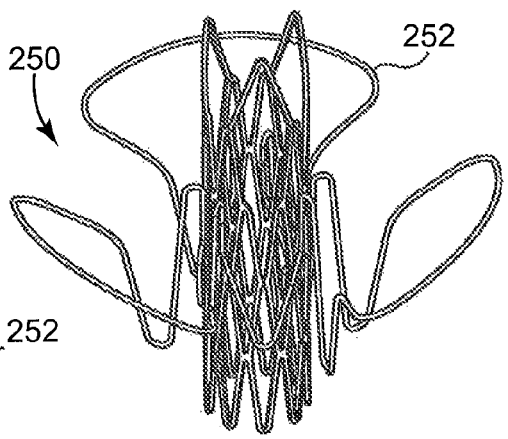
FIG. 47 is a perspective view of the stent of FIG. 46.
Figure 48:
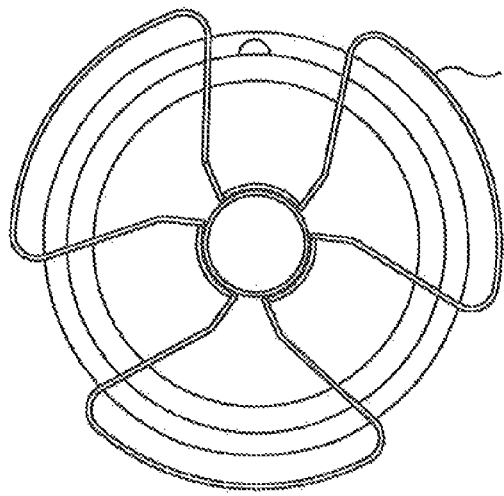
FIG. 48 is a top view of the stent of FIG. 47 positioned within a prosthetic heart valve, with the stent in its partially compressed state.
Figure 49:
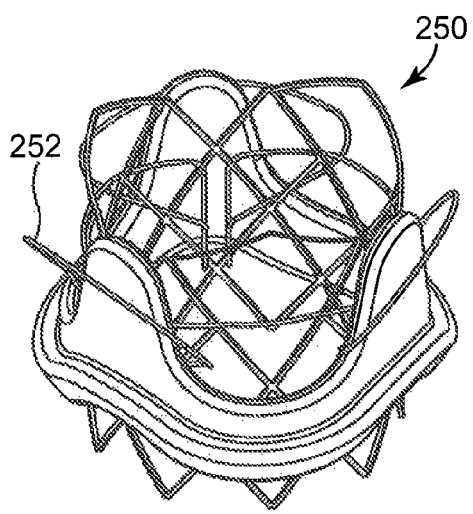
FIG. 49 is a perspective view of the stent of FIG. 47 in its expanded state as positioned within a prosthetic heart valve.
Figure 50:
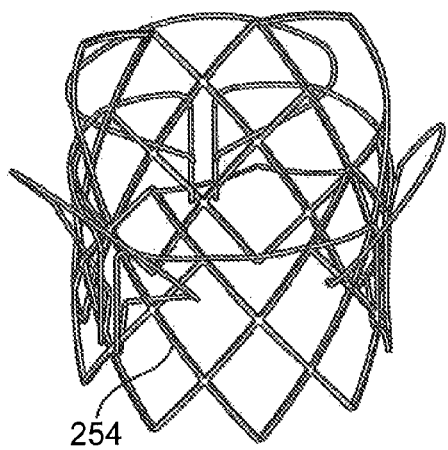
FIG. 50 is a perspective view of the stent of FIG. 47 in its expanded state.

FIGS. 23 and 24 illustrate another exemplary embodiment of a stent 140 for use as a replacement prosthetic heart valve in accordance with the invention. This stent 140 includes similar structures to that of the stent 30 of FIG. 1; however, stent 140 does not include lower vertical members that correspond to and extend in the opposite direction from upper vertical members 142. Otherwise, stent 140 can include any of the features described above relative to the stents of the invention. Stent 140 can be self-expanding or expandable with application of a radial force, and pericardial tissue or other materials may be attached to its structure to provide a prosthetic heart valve.

FIGS. 25-29 illustrate another exemplary embodiment of a stent 150 for use as a replacement prosthetic heart valve in accordance with the present invention. Stent 150 includes similar structures to the stent 110 of FIG. 11, including upper vertical members 152 and corresponding lower vertical members 154, stent post engagement structures 156, and lower flange members 158. In an embodiment where the number of stent post engagement structures 156 is optionally less than the number of corresponding stent posts of the previously implanted heart valve, upper flange members may be included on stent 150, if desired. Alternatively, upper flange members may be included on stent 150 in a configuration that does not interfere with the structures 156.

Stent 150 further includes "W" shaped structures 160 positioned along the stent ring 14 between adjacent stent posts 16 in the interior area of the stent structure 12. Each structure 160 is positioned generally between adjacent lower flange members 158 and provides additional contact surfaces between the stent 150 and the interior portion of the stent structure 12. In addition, any or all of the structures 160 can be used to hold a leaflet of the failed bioprosthesis against the stent ring of the failed bioprosthesis (such as stent ring 14) so that the leaflets of the failed bioprosthesis do not interfere with the valve leaflets of the newly implanted valved stent. That is, it may be desirable to hold the leaflets of the failed bioprosthesis toward the stent ring in order to minimize the potential for formation of thrombus between the failed leaflets and the new leaflets. In addition, holding the leaflets against the stent ring can prevent abrasion and/or tearing of the new leaflets that can occur during repeated contact with the old leaflets. The structures 160 may take a "W" type shape, as shown, or may instead have a different shape, such as one or more "U" or "V" shapes, a series of extensions, a sinusoidal shape, or any desired configuration that can hold leaflets against the stent ring of the failed bioprosthesis, when desired.

The stent 150 may comprise any desired number of components that are connected or attached to each other; however, the exemplary embodiment of stent 150 illustrated in FIG. 28 provides an embodiment with two separate structures attached or arranged relative to each other. That is, a first component is a formed structure that includes the stent post engagement structures 156 and the "W" shaped structures 160, while a second component is a formed structure that includes the upper and lower vertical members 152, 154 and the lower flange members 158.

FIGS. 30-34 illustrate another exemplary embodiment of a stent 170 for use as a prosthetic heart valve in accordance with the present invention. Stent 170 generally includes upper vertical members 172 and corresponding lower vertical members 174, upper flange members 176, lower flange members 178, and upper connecting members 182. In this embodiment, the upper flange members 176 are offset relative to lower flange members 178 such that each of the upper flange members 176 is positioned generally between adjacent stent posts 16 of stent structure 12, and each of the lower flange members 178 is generally aligned with the stent posts 16. Upper connecting members 182 extend between adjacent upper vertical members 172 and are provided for tying together the upper vertical members 172 to carry the valve hydrodynamic closing loads, which can thereby reduce various stresses in the stent. The upper connecting members 182 can also provide interface points for connection of the stent 170 with the delivery system used for the implantation process. Stent 170 further includes optional lower connecting members 184 that extend between adjacent lower vertical members 174. Lower connecting members 184 are provided for attachment of the material that makes up the leaflets of the replacement heart valve. That is, pericardial or another valve material may be sewn or otherwise attached to the lower connecting members 184 and may further be sewn or otherwise attached to the upper vertical members 172.

The upper connecting members 182 are shown as a single curved member; however, the connecting members can have any desired structure or configuration that provides the desired support for the upper vertical members 172. Further, the connecting members 182 may be made of the same or a different material than the other portions of the stent.

One or more of the lower flange members 178 may further include an eyelet or aperture 180 for engagement with a structure for use during the implantation of the stent 170 (e.g., sutures or a hook structure that can pull the stent structure toward its central axis). One or more of the upper vertical members 172 may similarly include an eyelet or aperture 185 for use during the implantation of the stent 170 and/or for use as an anchor point for attachment of valve material to the stent 170.

FIGS. 35-41 illustrate another exemplary embodiment of a stent 200 for use as a replacement prosthetic heart valve in accordance with the present invention. Stent 200 is similar to stent 120 of FIG. 16 in that stent 200 also includes a portion that is made of a material that is expandable (e.g., stainless steel) with a device such as a balloon catheter, for example, and a portion that is made of a material that is self-expanding (e.g., Nitinol) when external forces are removed. In particular, a self-expanding portion of stent 200 may include upper flange portions 202 that can be generally positioned between adjacent stent posts 16 of a stent structure 12, and bracing portions 204 that can be generally aligned with stent posts 16 of a stent structure 12. The other portion (i.e., the portion that is not self-expanding) of the stent 200 may include any or all of the following structures: upper vertical members 206; lower vertical members 208; upper support structures 210 extending between adjacent upper vertical members 206; lower support structures 212 extending between adjacent lower vertical members 208, lower flange portions 220; and intermediate lower flange portions 214 located between adjacent lower flange portions 220. The lower flange portions 214 can provide additional anchoring force for the stent 200 against the stent structure 12 in the areas generally adjacent to the stent posts 16. The lower support structures 212 may be used for securing the valve structure to the stent 200, if desired.

FIGS. 42-45 illustrate another exemplary embodiment of a stent 230 for use as a prosthetic heart valve in accordance with the present invention. Stent 230 includes multiple upper vertical members 232 and optional corresponding lower vertical members 234, and multiple lower flange members 236. The number of upper vertical members 232 and lower vertical members 234 preferably correspond to the number of stent posts of the previously implanted heart valve. In addition, the number of lower flange members 236 also preferably corresponds to the number of stent posts 16 of the previously implanted heart valve 10 so that one lower flange member 236 can be positioned generally between two adjacent stent posts 16, but on the opposite side of the stent structure 12 from the stent posts 16. The stent 230 further includes multiple upper flange members 238, which are positionable in the space between every two adjacent stent posts 16, but on the same side of the stent structure 12 as the stent posts 16. In this embodiment illustrated in FIGS. 42-45, two upper flange members 238 are positioned in each of the spaces between two adjacent stent posts 16, which thereby provide additional anchoring points for the stent 230 within the stent structure 12. In addition, these flange members 238 can function similarly to the structures 160 described above relative to FIGS. 25-29 in that one or more of the flange members 238 can help to hold the leaflets of the failed bioprosthesis generally against the stent ring of the bioprosthesis so that they do not interfere with the leaflets of the new valved stent. The stent 230 can be configured so that each of the upper flange members 238 of the pair of upper flange members are angled at least slightly toward their adjacent stent posts 16 so that they are facing in at least slightly opposite directions from each other.

FIGS. 46-50 illustrate another exemplary embodiment of a stent 250 for use as a prosthetic heart valve in accordance with the invention. Stent 250 is similar to stent 120 of FIG. 16 in that stent 250 also includes a portion that is made of an expandable material (e.g., stainless steel) with a balloon catheter, for example, and a portion that is made of a material that is self-expanding (e.g., Nitinol) when external forces are removed. In particular, a self-expanding portion of stent 250 may include multiple stent post engagement structures 252, which are shown in this embodiment as being part of a continuous unit or piece that is configured to include three stent post engagement structures 252. Each of the structures 252 is provided to engage with a stent post 16 of a stent structure 12. The other portion (i.e., the portion that is not self-expanding) of the stent 250 comprises a mesh-like stent structure 254 that includes a number of wire portions arranged as best illustrated in the expanded version of the stent 250 in FIG. 50. Although this embodiment does not illustrate particular flange portions that extend above or below the stent structure 12, it is contemplated that any of the anchoring structures discussed above may be incorporated into the stent 250 to provide additional anchoring mechanisms for the stent 250.

Figure 52:
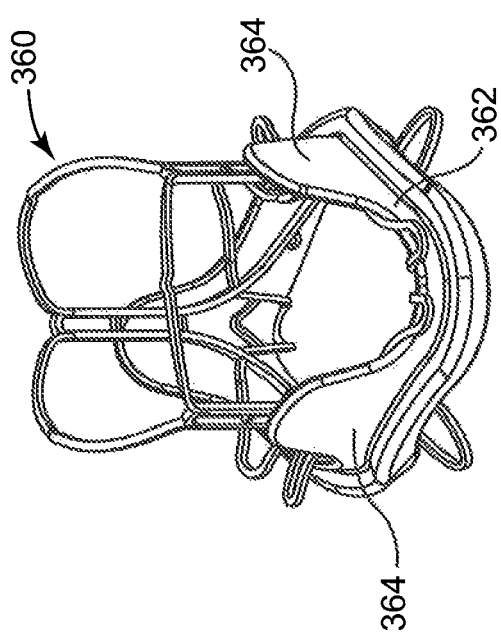
FIGS. 51 and 52 are perspective views of a prosthetic heart valve with a stent of a replacement prosthetic heart valve of the invention positioned therein, where FIG. 52 also shows the leaflets of the original prosthetic heart valve.
Figure 51:
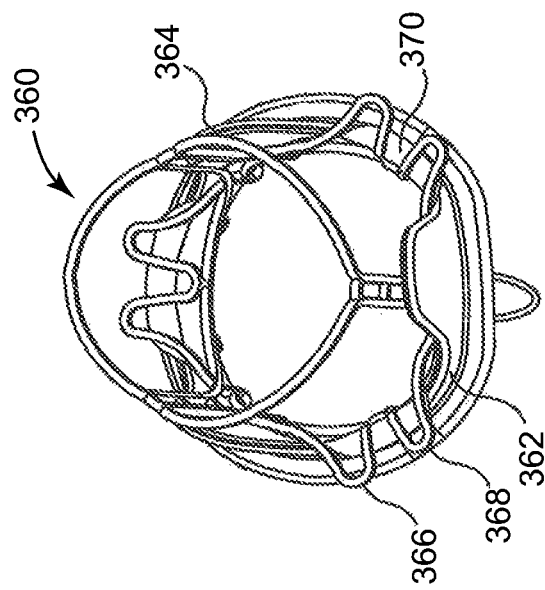

FIGS. 51 and 52 illustrate another stent 360 of the invention as it can be implanted within a previously implanted heart valve, such as a heart valve 362. FIG. 52 illustrates an exemplary positioning of the leaflets 370 of the previously implanted heart valve 362 and FIG. 51 does not show these leaflets. Stent 360 includes a split petal structure for its upper flange member that is positioned between stent posts 364, as shown with petals 366, 368. These petals 366, 368 provide two structures for holding the leaflets 370 of the heart valve 362 against the stent rail of that heart valve 362 so that the leaflets 370 do not interfere with the implantation and/or functioning of the newly implanted heart valve. The petals 366, 368 may have the same configuration as each other, as shown, or may instead be differently sized and/or shaped than each other. It is also contemplated that other structures may be used, such as a series of barbs or extending members, and it is further understood that more or less than two structures can be used for holding the leaflets 370 against the rail of the heart valve 362. The petal structures could also be used to hold native leaflets outward for the stented valve implanted in a native valve.

As discussed herein, the various stent embodiments of the invention can all be used with a valve structure for replacement of a previously implanted prosthetic heart valve. A number of different delivery systems can be used for implantation of such devices, including the delivery systems described above, along with other exemplary delivery systems, such as those described in U.S. Patent Application Publication No. 2003/0199963-A1; U.S. patent application Ser. No. 12/070,382, entitled "DELIVERY SYSTEMS AND METHODS OF IMPLANTATION FOR REPLACEMENT PROSTHETIC HEART VALVES", filed on even date herewith; U.S. patent application Ser. No. 12/070,380, entitled "DELIVERY SYSTEMS AND METHODS OF IMPLANTATION FOR REPLACEMENT PROSTHETIC HEART VALVES", filed on even date herewith, and U.S. patent application Ser. No. 12/070,347, entitled "REPLACEMENT PROSTHETIC HEART VALVES AND METHODS OF IMPLANTATION", filed on even date herewith, all of which are incorporated by reference in their entireties.

Referring again to FIG. 1, the stent or valve structure 12 includes a sewing ring 14 and stent posts 16 and is covered by a covering 18, such as is included in the stented tissue valves commercially available from Medtronic, Inc. of Minneapolis, Minn. under the trade designations "Hancock II" and "Mosaic". A wide variety of other stented tissue valves, such as those described in U.S. Pat. Nos. 4,680,031, 4,892,541, and 5,032,128, the teachings of which are incorporated herein by reference, can be employed as the stent or valve structure 12. Alternatively, the structure 12 can be stentless, such as, for example, a Freestyle stentless bioprosthesis, commercially available from Medtronic, Inc. under the trade designation "Freestyle". Other acceptable stentless configurations are described in U.S. Pat. Nos. 5,156,621; 5,197,979; 5,336,258; 5,509,930; 6,001,126; 6,254,436; 6,342,070; 6,364,905; and 6,558,417, the teachings of which are incorporated herein by reference. Regardless, the leaflets (not shown) are attached to the structure 12 by sewing, crimping, adhesive, etc., for example, and can assume a variety of forms (e.g., autologous tissue, xenograph tissue, or synthetic material, such as polymers, metals, combinations thereof, and the like).

With any of the embodiments of the invention described herein, the valved stents can be placed inside of a failed valve with leaflets, as described herein, or the leaflets of the failed valve can be removed prior to implantation of the new valved stents, in accordance with known procedures for leaflet removal. Exemplary procedures for leaflet removal are described, for example, in U.S. Patent Publication No. 2004/0034380 (Woolfson et al.), and exemplary devices and methods of filtering in conjunction with leaflet removal are described, for example, in U.S. Pat. No. 6,896,690 (Lambrecht et al.) and U.S. Pat. No. 6,692,513 (Streeter et al.), all of which are incorporated herein by reference. In this way, the leaflets of the failed bioprosthesis cannot interfere with the leaflets of the newly implanted valved stent and particulates from the leaflet removal can be filtered from the blood of the patient.

Stents described herein may further include at least one location of a radiopaque, echogenic, or MRI visible material to facilitate visual confirmation of proper placement of the stent relative to the previously implanted prosthetic heart valve. Alternatively, other known surgical visual aids can be incorporated into the stent. Such visual aids can be included on at least one flange of the replacement heart valve and at least one stent post of the previously implanted heart valve to provide indicators for proper placement of the stent.

It is further noted that the stent embodiments described herein can also include a tubular structure that is generally positioned within the previously implanted heart valve, wherein the various flanges and stent post engagement features can extend from the body of the tubular structure. In addition, the stents described herein may include a gasket material around all or a portion of the perimeter to provide for enhanced sealing between the new prosthetic valve and the previously implanted heart valve.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A replacement prosthetic heart valve for engagement with a structure of a previously implanted prosthetic heart valve, the replacement heart valve comprising:
   a stent structure comprising:
   a generally tubular body portion comprising an interior area;
   exactly three upper vertical members that are spaced apart from each other around a perimeter of the body portion and that extend in a direction that is generally parallel to a longitudinal axis of the body portion and each comprising one of a generally U-shaped and a generally V-shaped structure;

a plurality of lower vertical members that are spaced apart from each other around the perimeter of the body portion and that extend in a direction that is generally parallel to a longitudinal axis of the body portion and each comprising one of a generally U-shaped and a generally V-shaped structure;

a plurality of upper flange portions extending radially outwardly from the body for positioning at an outflow end of the previously implanted prosthetic heart valve and each comprising one of a generally U-shaped and a generally V-shaped structure between opposing, first and second ends, wherein the plurality of upper flange portions includes a first upper flange portion, and further wherein the first end of the first upper flange portion is attached to a first one of the upper vertical members and the second end of the first upper flange portion is attached to a second one of the upper vertical members such that only a single one of the plurality of upper flange portions is located between the first and second ones of the exactly three upper vertical members, and further wherein continuous extension of the first upper flange portion from the first one of the upper vertical members to the second one of the upper vertical members defines a single tip having a tighter curvature as compared to all other regions of the first upper flange portion; and at least one lower flange portion for positioning at the inflow end of the previously implanted heart valve, wherein at least one of the lower flange portions is attached at both of its first and second ends to the tubular body portion, extends outwardly from the tubular body portion, and comprises one of a generally U-shaped and a generally V-shaped structure; and at least two leaflets attached within the interior area of the tubular body portion of the stent structure.

2. The replacement heart valve of claim 1, wherein at least one of the generally tubular body portion and the plurality of upper flange portions is self-expandable from a collapsed position to an expanded position in response to removal of an external compressive force.

3. The replacement heart valve of claim 1, wherein the stent structure comprises at least one portion that is self-expandable with the removal of an external compressive force and at least one portion that is expandable with the application of an outward radial force.

4. The replacement heart valve of claim 3, wherein the tubular body portion comprises a material that is expandable with the application of an outward radial force.

5. The replacement heart valve of claim 1, wherein the at least one lower flange portion is biased toward an outflow end of the replacement heart valve.

6. The replacement heart valve of claim 1, wherein each of the plurality of upper flange portions is biased toward an inflow end of the replacement heart valve.

7. The replacement heart valve of claim 1, further comprising a visually detectable marker.

8. The replacement heart valve of claim 1, further comprising a sealing gasket surrounding at least a portion of a perimeter of the generally tubular body portion.

9. The replacement heart valve of claim 1, wherein each of the respective ones of the upper flange portions extends between two adjacent ones of the exactly three upper vertical members.

10. The replacement heart valve of claim 1, wherein one of the lower flange portions extends between two adjacent lower vertical members.

11. The replacement heart valve of claim 1, wherein one of the upper flange portions and one of the lower flange portions extend from a common area on the first one of the exactly three upper vertical members to a common area on the second one of the exactly three upper vertical members.

12. The replacement heart valve of claim 1, wherein each of the exactly three upper vertical members is longitudinally aligned with a corresponding one of the plurality of lower vertical members.

13. The replacement heart valve of claim 1, wherein:
the exactly three upper vertical members includes a first upper vertical member extending to and terminating at a tip opposite the plurality of lower vertical members;
the plurality of lower vertical members includes a first lower vertical member extending to and terminating at a tip opposite the exactly three upper vertical members;
the first upper vertical member is longitudinally aligned with the first lower vertical member;
the first upper flange portion is longitudinally aligned with the at least one lower flange portion;
and further wherein the stent structure is configured to self-retain an arrangement in which a longitudinal distance between the tip of the first upper vertical member and the tip of the first lower vertical member is greater than a longitudinal distance between the first upper flange portion and the at least one lower flange portion.

14. The replacement heart valve of claim 1, wherein the stent frame is configured to self-retain an arrangement in which each of the upper vertical members extend in a direction opposite the plurality of lower vertical members, and each of the lower vertical members extend in a direction opposite the upper vertical members.

15. The replacement heart valve of claim 1, wherein the stent structure defines a radial direction perpendicular to the longitudinal axis, and further wherein the stent structure is configured to self-retain an arrangement in which an extension of each of the plurality of upper flange portions relative to the longitudinal axis in the radial direction is greater than an extension of each of the upper vertical members relative to the longitudinal axis in the radial direction.

16. The replacement heart valve of claim 1, wherein the plurality of upper flange portions further includes a second upper flange portion, wherein the first end of the second upper flange portion is attached to the second one of the upper vertical members and the second end of the second upper flange portion is attached to a third one of the upper vertical members such that only a single one of the plurality of upper flange portions is located between the second and third ones of the exactly three upper vertical members.

17. The replacement heart valve of claim 16, wherein the plurality of upper flange portions further includes a third upper flange portion, wherein the first end of the third upper flange portion is attached to the third one of the upper vertical members and the second end of the third upper flange portion is attached to the first one of the upper vertical members such that only a single one of the plurality of upper flange portions is located between the first and third ones of the exactly three upper vertical members.

18. The replacement heart valve of claim 1, wherein each of the plurality of upper flange portions extends to and terminates at a tip, and further wherein each of the plurality of upper flange portions comprises a tighter curvature at the respective tip as compared to other regions of the respective upper flange portion proximate the respective tip.

19. A replacement prosthetic heart valve for engagement with a structure of a previously implanted prosthetic heart valve, the replacement heart valve comprising:
  a stent structure comprising:
    a generally tubular body portion comprising an interior area;
    exactly three upper vertical members that are spaced apart from each other around a perimeter of the body portion and that extend in a direction that is generally parallel to a longitudinal axis of the body portion;
    a plurality of upper flange portions extending radially outwardly from the body portion for positioning at an outflow end of the previously implanted prosthetic heart valve and each comprising one of a generally U-shaped and a generally V-shaped structure between opposing, first and second ends, wherein the plurality of upper flange portions includes a first upper flange portion, and further wherein the first end of the first upper flange portion is attached to a first one of the upper vertical members and the second end of the first upper flange portion is attached to a second one of the upper vertical members such that only a single one of the plurality of upper flange portions is located between the first and second ones of the exactly three upper vertical members; and
    a plurality of lower vertical members that are spaced apart from each other around the perimeter of the body portion and that extend in a direction that is generally parallel to the longitudinal axis of the body portion; and
    at least one lower flange portion for positioning at the inflow end of the previously implanted heart valve, wherein at least one of the lower flange portions is attached at both of its first and second ends to the tubular body portion, extends outwardly from the tubular body portion, and comprises one of a generally U-shaped and a generally V-shaped structure; and
  at least two leaflets attached within the interior area of the tubular body portion of the stent structure; and
  further wherein one of the upper flange portions and one of the lower flange portions extend from a common area on the first one of the exactly three upper vertical members to a common area on the second one of the exactly three upper vertical members.

* * * * *